US012575815B2

(12) United States Patent
Lampotang et al.

(10) Patent No.: US 12,575,815 B2
(45) Date of Patent: Mar. 17, 2026

(54) GUIDANCE AND TRACKING SYSTEM FOR TEMPLATED AND TARGETED BIOPSY AND TREATMENT

(71) Applicant: University of Florida Research Foundation, Inc., Gainesville, FL (US)

(72) Inventors: Samsun Lampotang, Gainesville, FL (US); David Erik Lizdas, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 920 days.

(21) Appl. No.: 17/437,096

(22) PCT Filed: Mar. 13, 2020

(86) PCT No.: PCT/US2020/022713
§ 371 (c)(1),
(2) Date: Sep. 8, 2021

(87) PCT Pub. No.: WO2020/186198
PCT Pub. Date: Sep. 17, 2020

(65) Prior Publication Data
US 2022/0133284 A1    May 5, 2022

Related U.S. Application Data

(60) Provisional application No. 62/817,726, filed on Mar. 13, 2019.

(51) Int. Cl.
*A61B 34/20* (2016.01)
*A61B 10/02* (2006.01)
(Continued)

(52) U.S. Cl.
CPC .......... *A61B 10/0241* (2013.01); *A61B 34/20* (2016.02); *A61B 34/25* (2016.02);
(Continued)

(58) Field of Classification Search
CPC ........ A61B 2010/0208; A61B 10/0241; A61B 2034/105; A61B 2034/107; A61B 34/20;
(Continued)

(56) References Cited

U.S. PATENT DOCUMENTS 4,613,328 A    9/1986 Boyd
5,704,791 A    1/1998 Gillio
(Continued)

FOREIGN PATENT DOCUMENTS

CN    103379853 A  * 10/2013 ............. A61B 5/318
EP    0696437 A2    2/1996
(Continued)

OTHER PUBLICATIONS

Extended European Search Report for European Patent Application No. 20769292.2, dated Oct. 26, 2022, (13 pages), European Patent Office, Munich, Germany.
(Continued)

*Primary Examiner* — Brian L Casler
(74) *Attorney, Agent, or Firm* — Alston & Bird LLP

(57)    ABSTRACT

Disclosed are various embodiments for a guidance and tracking system that facilitate templated and targeted biopsy and/or treatment. A guidance and tracking system may include a catheter having a six-degree-of-freedom magnetic tracking sensor, where the catheter can be positioned and anchored in an organ or a natural passage of an organ such as the urethral passage in the prostate of a patient. Using tracking sensors, a computing device may be employed to track a location and orientation of an organ and medical instruments during a treatment or diagnostic procedure. The computing device may determine a position and orientation of the medical instrument relative to the organ of interest. A graphical user interface including real, three-dimensional objects to overlay and adjust biopsy templates onto a real
(Continued)

Guidance and Tracking System 100

Ultrasound Machine 130

Patient in Left Lateral Decubitus Position

Catheter 105

Manual Segmentation & 3D Visualization Guidance Overlay

Magnetic Tracker 155

Prostate

Removable Output 135

Computing/ Device 115

Video Capture Device 150

Snap-on Retrofit 160a

Snap-on Retrofit 160b

TRUS Ultrasound Probe 120

Biopsy Gun 125

6DoF Tracking System 110 three-dimensional organ or lesion that is manually recon-structed prior to the biopsy procedure. A simulator or simulator mode can be provided for training.

20 Claims, 25 Drawing Sheets

(51) Int. Cl.
A61B 34/00 (2016.01)
A61B 34/10 (2016.01)
A61B 90/00 (2016.01)

(52) U.S. Cl.
CPC . *A61B 2010/0208* (2013.01); *A61B 2034/105* (2016.02); *A61B 2034/107* (2016.02); *A61B 2034/2048* (2016.02); *A61B 2034/2051* (2016.02); *A61B 2034/2065* (2016.02); *A61B 2090/365* (2016.02); *A61B 2090/371* (2016.02); *A61B 2090/3784* (2016.02)

(58) Field of Classification Search
CPC ...... A61B 2034/2065; A61B 2090/365; A61B 34/25; A61B 2090/367; A61B 2090/3784; A61B 2034/102; A61B 2034/104; A61B 2034/2051; A61B 2034/2048; A61B 2090/371; A61B 17/3403; A61B 2017/3413; A61B 5/06; A61B 90/37
USPC ........................................................ 600/424
See application file for complete search history.

(56) References Cited

U.S. PATENT DOCUMENTS

| | | | |
|---|---|---|---|
| 6,020,891 A | 2/2000 | Rekimoto | |
| 6,024,576 A | 2/2000 | Bevirt et al. | |
| 6,490,467 B1* | 12/2002 | Bucholz | A61B 8/5238 |
| | | | 600/407 |
| 6,561,980 B1 | 5/2003 | Gheng et al. | |
| 6,714,901 B1 | 3/2004 | Cotin et al. | |
| 6,842,175 B1 | 1/2005 | Schmalstieg et al. | |
| 6,857,878 B1 | 2/2005 | Chosack et al. | |
| 6,863,536 B1 | 3/2005 | Fisher et al. | |
| 7,130,447 B2 | 10/2006 | Aughey et al. | |
| 7,747,311 B2 | 6/2010 | Quaid, III | |
| 7,844,320 B2* | 11/2010 | Shahidi | A61B 5/06 |
| | | | 600/407 |
| 8,066,629 B2 | 11/2011 | Dlugos | |
| 8,425,418 B2 | 4/2013 | Suri et al. | |
| 8,948,845 B2 | 2/2015 | Glossop et al. | |
| 9,521,994 B2 | 12/2016 | Kamen et al. | |
| 9,626,805 B2 | 4/2017 | Lampotang et al. | |
| 9,681,919 B2 | 6/2017 | Glossop | |
| 10,026,191 B2 | 7/2018 | Accomando et al. | |
| 10,881,375 B2 | 1/2021 | Takimoto et al. | |
| 2002/0168618 A1 | 11/2002 | Anderson et al. | |
| 2003/0135115 A1 | 7/2003 | Burdette | |
| 2003/0220557 A1 | 11/2003 | Cleary et al. | |
| 2004/0064298 A1 | 4/2004 | Levine | |
| 2004/0097805 A1 | 5/2004 | Verard et al. | |
| 2004/0175684 A1 | 9/2004 | Kaasa et al. | |
| 2005/0084833 A1 | 4/2005 | Lacey et al. | |
| 2006/0008786 A1 | 1/2006 | Feygin et al. | |
| 2006/0099557 A1 | 5/2006 | Hyltander et al. | |
| 2006/0152516 A1 | 7/2006 | Plummer | |
| 2007/0016050 A1 | 1/2007 | Moehring et al. | |
| 2007/0060391 A1 | 3/2007 | Ikeda et al. | |
| 2007/0236514 A1 | 10/2007 | Agusanto et al. | |
| 2008/0070684 A1 | 3/2008 | Haigh-Hutchinson | |
| 2008/0171311 A1 | 7/2008 | Centen et al. | |
| 2008/0172119 A1 | 7/2008 | Yamasaki et al. | |
| 2008/0187896 A1 | 8/2008 | Savitsky | |
| 2008/0200926 A1 | 8/2008 | Verard et al. | |
| 2008/0287794 A1 | 11/2008 | Li et al. | |
| 2009/0093715 A1 | 4/2009 | Downey et al. | |
| 2009/0326556 A1 | 12/2009 | Diolaiti et al. | |
| 2010/0036199 A1 | 2/2010 | Karasawa et al. | |
| 2010/0159434 A1 | 6/2010 | Lampotang et al. | |
| 2010/0167249 A1 | 7/2010 | Ryan | |
| 2010/0167250 A1 | 7/2010 | Ryan et al. | |
| 2010/0172559 A1 | 7/2010 | Kumar et al. | |
| 2010/0225340 A1 | 9/2010 | Smith et al. | |
| 2010/0298705 A1 | 11/2010 | Pelissier et al. | |
| 2010/0312100 A1* | 12/2010 | Zarkh | G06T 7/32 |
| | | | 382/128 |
| 2011/0046483 A1 | 2/2011 | Fuchs et al. | |
| 2011/0091855 A1 | 4/2011 | Miyazaki | |
| 2011/0170752 A1 | 7/2011 | Martin et al. | |
| 2011/0227913 A1 | 9/2011 | Hyndman | |
| 2012/0038639 A1 | 2/2012 | Mora et al. | |
| 2012/0259209 A1 | 10/2012 | Harhen | |
| 2013/0090554 A1* | 4/2013 | Zvuloni | A61B 5/061 |
| | | | 600/424 |
| 2013/0116548 A1* | 5/2013 | Kumar | A61B 8/12 |
| | | | 600/424 |
| 2013/0323700 A1 | 12/2013 | Samosky et al. | |
| 2013/0330701 A1 | 12/2013 | Rubinstein et al. | |
| 2014/0071165 A1 | 3/2014 | Tuchschmid et al. | |
| 2015/0125840 A1 | 5/2015 | Pastrick et al. | |
| 2015/0245825 A1* | 9/2015 | Stone | A61B 8/463 |
| | | | 600/567 |
| 2016/0133056 A1 | 5/2016 | Lampotang et al. | |
| 2017/0020623 A1* | 1/2017 | Glossop | A61B 90/11 |
| 2017/0221387 A1 | 8/2017 | Lampotang et al. | |
| 2017/0372640 A1 | 12/2017 | Lampotang et al. | |
| 2021/0134068 A1 | 5/2021 | Lampotang et al. | |
| 2021/0343186 A1 | 11/2021 | Lampotang et al. | |

FOREIGN PATENT DOCUMENTS

| | | | |
|---|---|---|---|
| EP | 1533683 A2 | 5/2005 | |
| EP | 1858418 B1 | 8/2017 | |
| JP | 2002-500941 A | 1/2002 | |
| JP | 2003-210386 A | 7/2003 | |
| JP | 2005-525598 A | 8/2005 | |
| JP | 2006201092 A | 8/2006 | |
| JP | 5416900 B2 | 2/2014 | |
| JP | 2017080501 A | 5/2017 | |
| KR | 2003-0044909 A | 6/2003 | |
| KR | 2003-0083695 A | 10/2003 | |
| KR | 1007-48269 B1 | 8/2007 | |
| WO | WO-1997/023172 A2 | 7/1997 | |
| WO | WO-1999/038141 A1 | 1/1999 | |
| WO | WO-1999/042978 A1 | 8/1999 | |
| WO | WO-2002/059859 A1 | 8/2002 | |
| WO | WO-2003/096307 A1 | 11/2003 | |
| WO | WO-2009/049282 A2 | 4/2009 | |
| WO | WO-2009/094646 A2 | 7/2009 | |
| WO | WO-2011/127379 A2 | 10/2011 | |
| WO | 2013155156 A1 | 10/2013 | |
| WO | WO 2015131162 A2 | 9/2015 | |
| WO | WO-2016/007717 A1 | 1/2016 | |

OTHER PUBLICATIONS

Markert, Mathias. Mathias Markert—Entwicklung Eines Kliniktauglichen Assistenzsystems Für Die Leberchirurgie, Doc-toral Dissertation, Technische Universität München, Jan. 31, 2011, (133 pages), XP055634184, available online: https://mediatum.ub.tum.de/doc/1007285/file.pdf.

Bichlmeier, Christoph et al. *Contextual Anatomic Mimeses: Hybrid In-Situ Visualization Method for Improving Multi-Sensory Depth Perception in Medical Augmented Reality*, ISMAR, 6th IEEE and ACM International Symposium on Mixed and Augmented Reality, (2007), (10 pages).

Bichlmeier, Christoph et al. *Improving Depth Perception in Medical AR: A Virtual Vision Panel to the Inside of the Patient*, Bildverabeitung für die Medizin, Springer Berlin Heidelberg, (2007), pp. 217-221.

Final Office Action for U.S. Appl. No. 13/514,474, filed Dec. 3, 2014, (33 pages), U.S. Patent and Trademark Office, USA.

(56)           References Cited

OTHER PUBLICATIONS

Final Office Action for U.S. Appl. No. 14/980,891, filed Aug. 23, 2016, (13 pages), U.S. Patent and Trademark Office, USA.
Final Office Action for U.S. Appl. No. 15/485,404, filed Jul. 27, 2018, (22 pages), U.S. Patent and Trademark Office, USA.
Final Office Action for U.S. Appl. No. 15/485,404, filed Jun. 13, 2019, (28 pages), U.S. Patent and Trademark Office, USA.
Final Office Action for U.S. Appl. No. 15/485,404, filed Jun. 16, 2020, (30 pages), U.S. Patent and Trademark Office, USA.
Final Office Action for U.S. Appl. No. 15/485,404, filed Sep. 20, 2017, (24 pages), U.S. Patent and Trademark Office, USA.
Fuhrmann, Anton et al. *Concept and Implementation of a Collaborative Workspace for Augmented Reality*, Graphics'99, vol. 18, No. 3, (1999), pp. 1-11.
Gallo, Luigi et al. *3D Interaction With Volumetric Medical Data Experiencing the Wiimote. Proceedings of the 1st International Conference on Ambient Media and Systems*, ICST (Institute for Computer Sciences, Social-Informatics and Telecommunications Engineering), 2008, (6 pages).
Goksel, Orcun et al. *B-Mode Ultrasound Image Simulation in Deformable 3D Medium*, IEEE Transactions on Medical Imaging, Mar. 2009, vol. 28, No. 11, pp. 1657-1669.
Hinckley, Ken et al. *Two-Handed Virtual Manipulation*, ACM Transactions on Computer-Human Interaction, vol. 5, No. 3, Sep. 1998, pp. 260-302.
Hu, John et al. *Effectiveness of Haptic Feedback in Open Surgery Simulation and Training Systems*, Studies in Health Technology and Informatics, vol. 119 (2006), pp. 213-218.
International Searching Authority, International Search Report and Written Opinion for International Application No. PCT/US2016/012861, May 2, 2016, 16 pages, Korean Intellectual Property Office, Republic of Korea.
International Searching Authority, International Search Report and Written Opinion for International Application No. PCT/US2011/031738, Feb. 8, 2012, (6 pages), Korean Intellectual Property Office, Republic of Korea.
Knudsen, Bodo E. et al. *A Randomized, Controlled, Prospective Study Validating the Acquisition of Percutaneous Renal Collecting System Access Skills Using a Computer Based Hybrid Virtual Reality Surgical Simulator: Phase I, The Journal of Urology*, Nov. 2006, vol. 176, No. 5, pp. 2173-2178. DOI: 10.1016/j.juro.2006.07.011.
NonFinal Office Action for U.S. Appl. No. 13/514,474, filed May 12, 2015, (25 pages), U.S. Patent and Trademark Office, USA.
NonFinal Office Action for U.S. Appl. No. 13/514,474, filed May 2, 2014, (23 pages), U.S. Patent and Trademark Office, USA.
NonFinal Office Action for U.S. Appl. No. 14/980,891, filed Apr. 27, 2016, (27 pages), U.S. Patent and Trademark Office, USA.
NonFinal Office Action for U.S. Appl. No. 15/485,404, filed Feb. 5, 2020, (20 pages), U.S. Patent and Trademark Office, USA.
NonFinal Office Action for U.S. Appl. No. 15/485,404, filed Jan. 24, 2018, (17 pages), U.S. Patent and Trademark Office, USA.
NonFinal Office Action for U.S. Appl. No. 15/485,404, filed Jan. 18, 2019, (21 pages), U.S. Patent and Trademark Office, USA.
NonFinal Office Action for U.S. Appl. No. 15/485,404, filed May 26, 2017, (25 pages), U.S. Patent and Trademark Office, USA.
NonFinal Office Action for U.S. Appl. No. 15/485,404, filed Sep. 25, 2019, (20 pages), U.S. Patent and Trademark Office, USA.
NonFinal Office Action for U.S. Appl. No. 15/538,990, filed Jan. 9, 2020, (7 pages), U.S. Patent and Trademark Office, USA.
NonFinal Office Action for U.S. Appl. No. 15/538,990, filed Sep. 16, 2020, (15 pages), U.S. Patent and Trademark Office, USA.

Notice of Allowance for U.S. Appl. No. 13/514,474, filed Sep. 25, 2015, (9 pages), U.S. Patent and Trademark Office, USA.
Notice of Allowance for U.S. Appl. No. 14/980,891, filed Dec. 13, 2016, (5 pages), U.S. Patent and Trademark Office, USA.
Notice of Allowance for U.S. Appl. No. 15/485,404, filed Sep. 17, 2020, (7 pages), U.S. Patent and Trademark Office, USA.
*PERC Mentor: Computerized Training Simulator for Percutaneous Access Puncturing*, Users Manual for the Combined PERC Mentor™M & URO Mentor™ Simulator, Version 2.03, Feb. 2003, Simbionix Computer Assisted Endoscopy, (33 pages).
Quarles, John et al. *A Mixed Reality Approach for Merging Abstract and Concrete Knowledge*, Proceedings of IEEE Virtual Reality, Feb. 2008, pp. 27-34, Reno, Nevada, USA.
Quarles, John et al. *Collocated AAR: Augmenting After Action Review With Mixed Reality*, 7th IEEEA/ACM ISMAR, Sep. 2008, pp. 1-10, Cambridge, United Kingdom.
Quarles, John et al. *Tangible User Interfaces Compensate for Low Spatial Cognition*, Proceedings of IEEE Symposium on 3D User Interfaces, Mar. 2008, pp. 11-18, Reno, Nevada, USA.
Stoev, Stanislav L. *Two-Handed Through-The-Lens-Techniques for Navigation in Virtual Environments*, Immersive Projection Technology and Virtual Environments, (2001), pp. 51-60, Springer Vienna.
Wignall, Geoffrey R. et al. *Surgical Simulation: A Urological Perspective*, The Journal of Urology, May 2008, vol. 179, No. 5, pp. 1690-1699. DOI: 10.1016/j.juro.2008.01.014.
Zhu, Yanong et al. *A Virtual Ultrasound Imaging System for the Simulation of Ultrasound-Guided Needle Insertion Procedures*, In Proceedings of Medical Image Understanding and Analysis (MIUA), Jul. 2006, pp. 61-65.
Markert, Mathias. "Development of a Clinically Suitable Assistance System for Liver Surgery," Doctoral Dissertation, Technical University of Munich, Jan. 31, 2011, (149 pages).
Non-Final Office Action for Japanese Application No. 2021-554731, dated Nov. 2, 2023, 12 pages.
International Search Report and Written Opinion for International Application No. PCT/US2020/022713 mailed Jun. 3, 2020.
Chen VH, Mouraviev V, Mayes JM, et al. "Utility of a 3-Dimensional Transrectal Ultrasound-guided Prostate Biopsy System for Prostate Cancer Detection," Technology in Cancer Research & Treatment (Apr. 2009), doi:10.1177/153303460900800202.
Megwalu, I. I., Ferguson, G. G., Wei, J. T., Mouraviev, V. , Polascik, T. J., Taneja, S. , Black, L. , Andriole, G. L. and Kibel, A. S. (2008), "Evaluation of a Novel Precision Template—Guided Biopsy System for Detecting Prostate Cancer," BJU International, 102: 546-550.
Han, Misop et al. *Geometric Evaluation of Systematic Transrectal Ultrasound Guided Prostate Biopsy*, The Journal of Urology, vol. 188, No. 6, Dec. 2012, pp. 2404-2409, DOI: 10.1016/j.juro.2012.07.107, (NIH Public Access, Author Manuscript, Dec. 31, 2013).
Hanna, Nawar et al. *Multiparametric Magnetic Resonance Imaging-Ultrasound Fusion Biopsy Improves but Does Not Replace Standard Template Biopsy for the Detection of Prostate Cancer*, The Journal of Urology, vol. 202, No. 5, Nov. 2019, pp. 944-951.
Lampotang, Samsun et al. *Baseline Prevalence and Magnitude of Spatial Deviations in a Simulator from the Transrectal Ultrasound Prostate Biopsy Template*, The Journal of Urology, vol. 201, Issue Supplement 4, May 4, 2019, pp. e503-e504.
Rosenkrantz, Andrew B. et al. *Evolving Use of Prebiopsy Prostate Magnetic Resonance Imaging in the Medicare Population*, The Journal of Urology vol. 200, No. 1, Jul. 1, 2018, pp. 89-94.

\* cited by examiner

Manual Tracing on
Ultrasound Image
Overlay

Traces are Saved
in 3D Space

Processed Traces...

...Are Used to Build a 3D
Object

400

BASE

LEFT
*MID GLAND*

RIGHT
*MID GLAND*

APEX

PA View

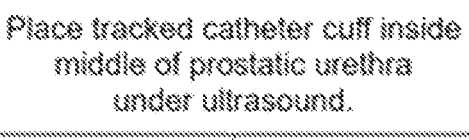

Place tracked catheter cuff inside
middle of prostatic urethra
under ultrasound.

Identify mid-sagittal landmarks (entry and exit of prostatic
urethra) in ultrasound. Mark reference landmarks on US image
via touchscreen. Save reference landmarks to prostate sensor
space. Save TRUS probe position.

Identify transverse reference landmarks in ultrasound. Mark
reference landmarks on US image via touchscreen. Save
landmarks to prostate sensor space. Save TRUS probe position.

Reference Landmarks in prostate sensor space compared to
their counterparts in live US images automatically or manually at
set intervals in time.
If slip automatically detected, or if time interval reached Prompt user to guide probe back to view containing
reference landmarks and display reference landmark
overlays Do reference landmarks overlay anatomical
landmarks?

Yes                     No

Continue procedure.
Prostate tracking sensor
is still in place.

Prostate tracking
sensor slipped.
Check cuff pressure,
rebuild or adjust 3D
prostate to match US
views.

*FIG. 16*

☐ TEMPLATE Bx CORE CENTERS
☒ GUIDED Bx CORE CENTERS

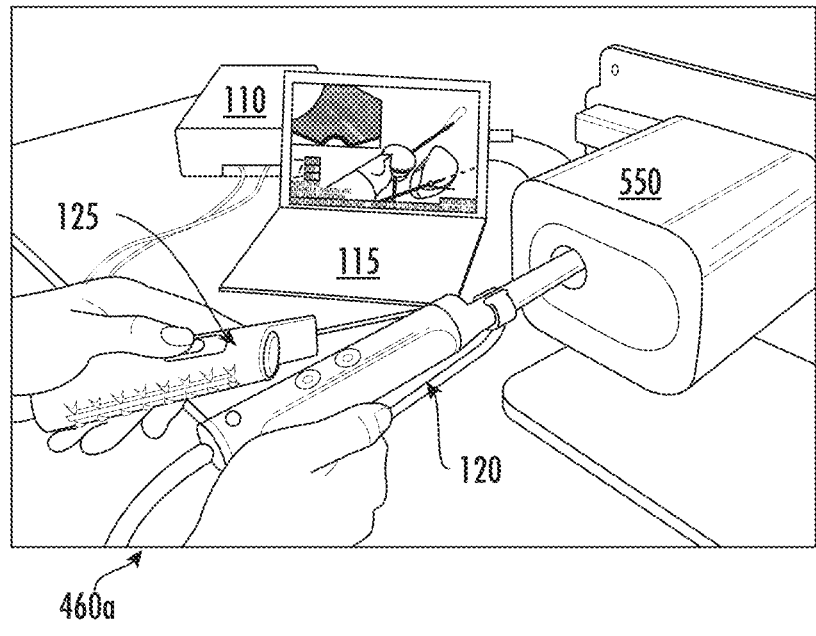
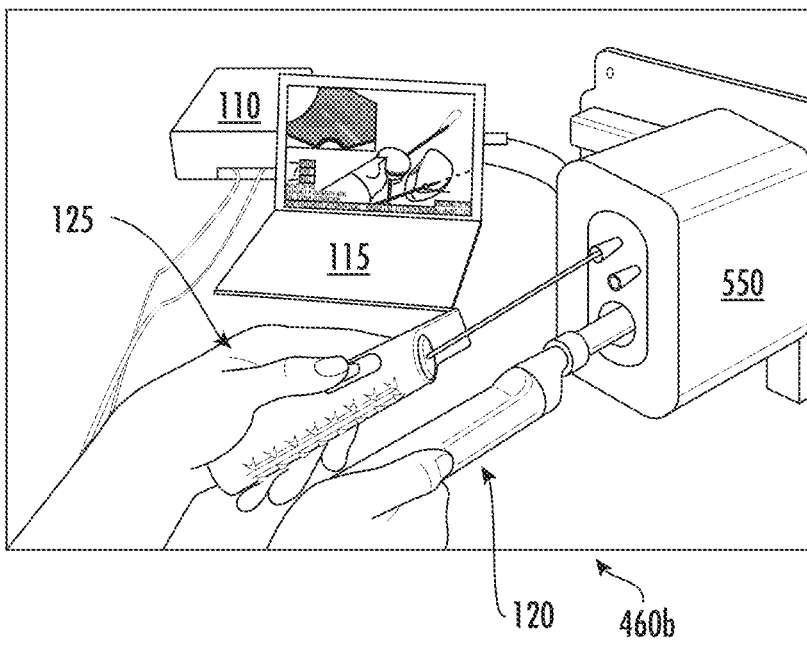
FIG. 26

GUIDANCE AND TRACKING SYSTEM FOR TEMPLATED AND TARGETED BIOPSY AND TREATMENT

CROSS-REFERENCE TO RELATED APPLICATIONS

This application is a national phase application under 35 U.S.C. § 371 of International Application No. PCT/US2020/022713 filed Mar. 13, 2020, entitled "GUIDANCE AND TRACKING SYSTEM FOR TEMPLATED AND TARGETED BIOPSY AND TREATMENT," which claims the benefit of and priority to U.S. Provisional Patent Application No. 62/817,726 entitled "GUIDANCE AND TRACKING SYSTEM FOR TEMPLATED AND TARGETED BIOPSY AND TREATMENT," filed Mar. 13, 2019, the contents of which being incorporated by reference in their entirety herein.

BACKGROUND

A biopsy involves removing tissue from a living body to discover the presence, cause, or extent of a disease by examination of the removed (biopsied) tissue. For instance, a breast or prostate biopsy can be performed to analyze a tissue for the presence of cancer cells. A needle biopsy uses a needle to obtain tissue or fluid samples from muscles, bones, and other organs, such as the liver, lungs, hips, and prostate for laboratory testing. Common needle biopsy procedures include fine-needle aspiration (e.g., amniocentesis) and core needle (e.g., prostate) biopsy. As such, a biopsy is a diagnosis tool, different from a treatment tool. Treatment is for therapy (not diagnosis), and may include placing radioactive or other seeds; medication, such as local anesthetics or steroids; heat; electricity; radiation; and so forth to specific targets in the body. Treatment can also include placing a needle tip in an abscess to obtain access to the abscess and drain fluid therefrom.

For both biopsy and treatment, accuracy is important. Inaccuracy may cause healthy tissue to be biopsied instead of cancerous tissue leading to a false negative or, in other words, cancer being present, but not sampled (biopsied) and a false negative diagnosis that cancer is not present being delivered. Inaccuracy may cause the treatment to be administered or placed at the wrong location. Other types of guided intervention procedures involve using imaging to guide at least one tool to a target or template location. Examples of such procedures include ablation, abscess drainage like paracentesis, aspiration (e.g., fine needle aspiration), biopsies, blocks (e.g., regional anesthetic blocks), venous access (e.g., central and peripheral venous access), among many others. "Sampling" as used herein can refer to sampling and/or treatment when referring to actions or locations.

Prostate cancer (PCa) is one of the most common types of cancer in men. As of 2018, prostate cancer is the second leading cause of death among men in the United States caused by cancer. In most cases, a doctor or other medical practitioner will not begin treatment for prostate cancer until a positive diagnosis is obtained via a pathology of biopsied samples that include cancerous tissue/cells obtained from the prostate. However, the collection of samples in a biopsy is often flawed, thereby resulting in false negatives which, of concern, can have an incidence or proportion as high as 47% for traditional TransRectal UltraSound (TRUS) guided prostate biopsy (PBx). Han et al., "Geometric Evaluation of Systematic Transrectal Ultrasound Guided Prostate Biopsy, J Urol. 188:2404-2409 (December 2012) established that experienced urologists have large template deviations during systematic prostate biopsy. Lampotang et al., "Baseline Prevalence and Magnitude of Spatial Deviations in a Simulator from the Transrectal Ultrasound Prostate Biopsy Template," Journal of Urology, Vol. 201, No. 4S, Supplement (May 2019) has shown that residents also have large template deviations that are similar to experienced urologists. Hanna et al., "Multiparametric MRI/Ultrasound Fusion Biopsy Improves but Does Not Replace Standard Template Biopsy for the Detection of Prostate Cancer," Journal of Urology, 202(5):944-951 (November 2019), has shown that sPBx is still useful in spite of the availability of fPBx. sPBx following fPBx detected 16% more PCa that would have been missed by fPBx. Lampotang et al. has shown that template deviation is related to PBxFN and that for a spherical lesion 1 cm in diameter at the apex, PBxFN is eliminated if the template deviation is below 5 mm, a threshold that Lampotang et al have suggested.

As an example of flaws with traditional TRUS biopsy, an actual biopsy sample may not have been collected at the recommended location when using a template. A template maps the spatial distribution of the biopsy samples so that the samples are uniformly distributed, attempting to ensure that areas where PCa is most likely present are sampled. A false negative invariably adds in the United States a delay of at least six months to initiation of PCa treatment because current practice is to wait at least six months after a biopsy before obtaining another PSA test that would prompt a repeat biopsy if the latest PSA value remains high or increases. Thus, a false negative can delay treatment of a patient with undiagnosed prostate cancer by six to nine months or more. During this time, the prostate cancer can grow and spread and the probability of being treated or cured is reduced. Further, there is no guarantee that a repeat of traditional TRUS PBx will not result in yet another false negative. Early PCa diagnosis via PBx offers more options for treatment or cure.

Systematic prostate biopsy (sPBx) uses a template and the presence or location of a lesion is not known. There is no target. The template locations in a sPBx template are not targets. The template locations help distribute the biopsy cores evenly around the prostate to reduce the risk of not sampling an entire prostate region where, in a worst case scenario, the non-sampled area contains a clinically significant prostate cancer (csPCa) lesion, leading to a prostate biopsy false negative (PBxFN). In targeted PBx, such as fusion prostate biopsy (fPBx), the lesion or a shadow or region of interest (ROI) has been identified by MRI and segmented (e.g., three-dimensionally reconstructed). As the name implies, in targeted PBx, there is a target (such as a ROI) unlike sPBx.

Notably, false negatives in prostate biopsies occur when only healthy regions of the prostate are sampled by a urologist or other medical practitioner. In other words, a cancerous region exists in a prostate; however, if tissue is collected only from outside of the cancerous region (i.e., only healthy tissue is collected), a prostate biopsy may return a false negative indicating that the patient is free of cancer when, in reality, that is not the case. Because treatment is only performed upon a positive diagnosis via prostate biopsy, false negatives unnecessarily delay treatment which, in turn, may give time for localized prostate cancer to metastasize and spread to nerve bundles that affect potency and bones, thereby reducing options, complicating treatment, and affecting quality of life of patients and survivors.

Recently, accurate PBx techniques, like the UroNav, require an MRI prior (generally a week before) to a fusion PBx, radiologist fees to interpret the MRI, the financial burden of an additional clinic visit (lost wages from another missed work day, transportation, and for rural patients, potentially lodging costs), and, more importantly, may not be covered for biopsy-naïve patients or by payers like Medicare/Medicaid (exacerbating health disparities (HD) by denying precision PBx to HD patients). Rosenkrantz et al., "Evolving Use of Prebiopsy Prostate Magnetic Resonance Imaging in the Medicare Population," Journal of Urology 200:89-94, (July 2018) showed substantial racial and geographic variations in pre-PBx MRI in Medicare patients indicative of HD.

U.S. Pat. No. 8,948,845 to Glossop defines a "patient space" as the coordinate system derived from a position sensor in an enhanced urinary catheter. An "image space" is defined as the coordinate system of the imaging modality, usually magnetic resonance imaging (MM), including using MRI imaging coils internal to the urinary catheter. Both the internal preoperative diagnostic images and the external preoperative diagnostic images are referred to as "image space data" (or may be used to obtain image space data), where internal refers to an internal MRI coil. The method of co-locating ("registering") the image space data to the patient space data requires the image space data (MRI data) to be gathered while the enhanced urinary catheter is inserted in the patient, and that at least some part of the catheter is visible in the MM imaging modality. In practical terms that are logistically significant in clinical settings, in the Glossop approach, the biopsy including the segmentation cannot be performed by a single urologist in a single visit to a urology clinic. The Glossop patent, according to its description, is similar to commercially available fused MRI/US prostate biopsy systems, whereby the patient has to obtain an MRI a week or so prior to the actual biopsy and requires the expense of a radiologist to interpret the MM. As a reference point, in the UroNav fused biopsy system, at the time of the biopsy, a significant amount of time (30-45 minutes and up) is required to manually fuse the MM scan with the ultrasound image.

U.S. Pat. No. 9,626,805 to Lampotang discusses a mixed reality simulator technology that is now applied for a mixed reality prostate biopsy (PBx) simulator that supports different PBx techniques: side-fire, end-fire, cognitive fusion, transperineal and fused biopsy among others. In the PBx simulator, a physical 3D prostate is tracked that floats in a soft enclosure/cradle by inserting an electromagnetic sensor (such as a 6-DOF tracking sensor) inside the prostate. This technique of tracking a movable organ is not specific to a prostate, but would be applicable to other organs that move in response to being pushed if forces are applied to them such as for example from an ultrasound probe or needle or manual manipulation.

BRIEF SUMMARY OF INVENTION

Various embodiments are disclosed for a guidance and tracking system for guided interventions including templated or targeted biopsy and/or treatment. More specifically, a three-dimensional tracking, guidance, and visualization system for precision biopsy and precision treatment is described that can use prostate biopsy and radiofrequency (RF) ablation respectively in some embodiments. In one embodiment, a non-fused tracking and guidance system includes a body organ tracking sensor, such as a prostate tracking sensor; a tracked medical imaging probe, such as an ultrasound probe, a tracked biopsy or treatment device for tracking the biopsy or treatment device in relation to the prostate and imaging probe, such as a tracked biopsy gun; and at least one computing device.

The at least one computing device can include program instructions stored in memory thereon that, when executed, direct the at least one computing device to: provide guidance associated with a position and an orientation of the tracked medical imaging probe to generate a plurality of images of an organ, where the position and the orientation of the tracked medical imaging probe (e.g., transrectal ultrasound probe) are determined using the body organ tracking sensor; generate a three-dimensional reconstruction of the organ or body part using the plurality of images; cause the three-dimensional reconstruction of the organ or body part and a virtual template comprising one or a plurality of sampling regions to be superimposed on the organ to be shown in a display device including as a 3D visualization; and provide guidance for a collection of tissue at one or each of the plurality of sampling regions, whether templated (for systematic or templated PBx) or targeted (for fused PBx).

The plurality of images can include two-dimensional ultrasound images in some embodiments. At least one of the plurality of two-dimensional ultrasound images can be shown in the display device contemporaneously with the three-dimensional reconstruction of the organ, the template and the 3D visualization of the prostate space that includes 3D visualization of the TRUS probe and 3D visualization of the biopsy device. The organ can include a prostate and the guidance for the collection of tissue is performed during a prostate biopsy procedure and the virtual template can include prostate biopsy cores as generally cylindrical 3D objects or the center of the prostate biopsy cores as 3D points or spheres.

In some embodiments, the three-dimensional reconstruction of the organ or body part is generated using a tracking sensor positioned outside of a body of a patient having the organ. The body organ tracking sensor can include an electromagnetic tracking sensor having six degrees-of-freedom (6-DOF). The guidance associated with the position and the orientation of the tracked medical imaging probe to generate the plurality of images of the organ can be provided based at least in part on a tracking of a catheter positioned in a patient having the organ, or a tracking of a sensor located external from the patient, including on the skin of the patient or in accessible orifices and cavities of the patient. The three-dimensional reconstruction of the organ or body part can include a three-dimensional reconstruction of one or more lesions or regions of interest (ROI) detected on or around the organ or body part.

The at least one computing device can be further directed to perform at least one of: adjusting core or template location (center of a core) locations and orientations, adjusting a number of cores, and changing a sequence of cores in a custom template. The guidance for the collection of tissue at one or each of the plurality of sampling regions can be provided without an imaging modality in some embodiments. For instance, an imaging modality is not needed during a biopsy or a treatment applied using the three-dimensional visualization, once the 3D reconstruction and the template fitting to the 3D reconstructed organ has been performed.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

FIG. 16 is a process for monitoring and detecting in real time if a tracked catheter slips or dislodges relative to the prostate

FIG. 26 is a photograph of the simulator being used to practice transperineal and transrectal techniques in accordance with various embodiments of the present disclosure.

DETAILED DESCRIPTION

Figure 5:
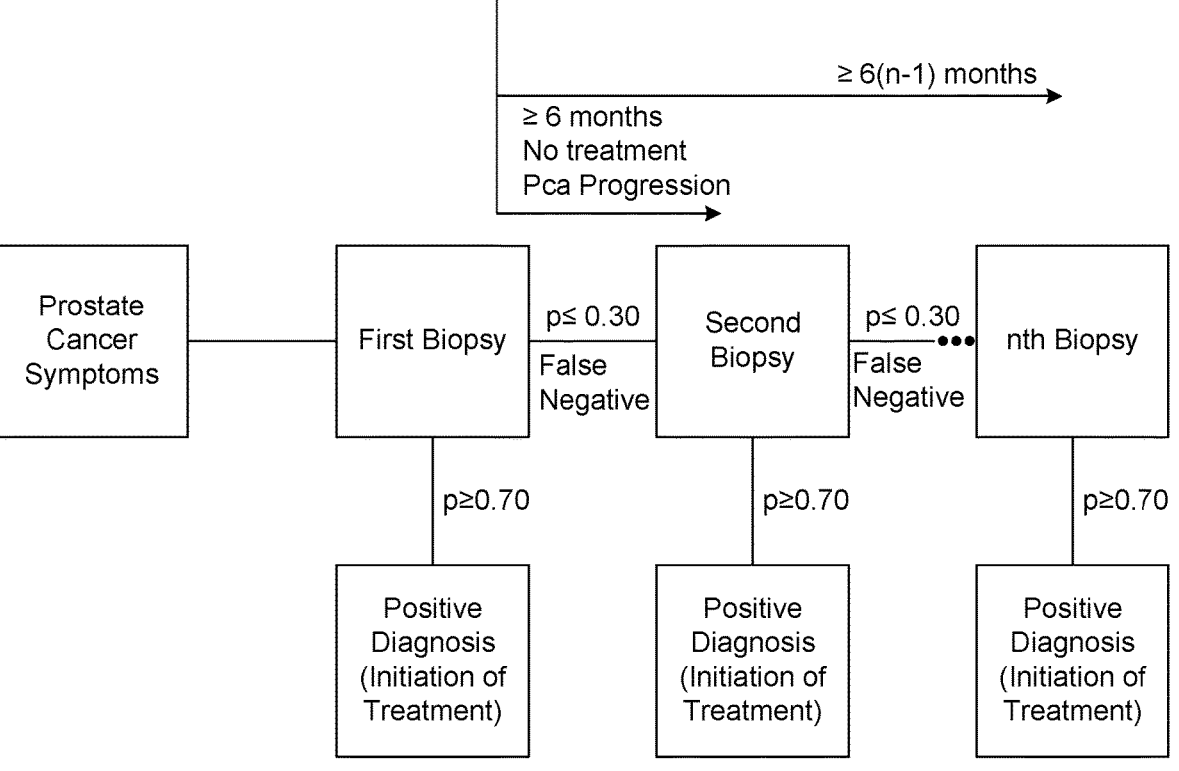
FIG. 5 is a diagram illustrating evolution over time of biopsy, diagnosis, and treatment for prostate cancer, along with the delay in initiating treatment introduced by prostate biopsy false negative rates of diagnoses.

The present disclosure relates to a guidance and tracking system for templated and targeted biopsy and treatment and guided interventions as well as associated apparatuses and methods associated therewith. Some groups, such as African-American men, tend to have a high-risk prostate cancer (PCa) rate and may have outcomes worse than those compared to that of other groups, e.g., the 2017 age-adjusted PCa mortality for blacks is 2.4 that of whites (Taksler 2012). PBx false negatives have been determined to be as high as 47% in traditional transrectal ultrasound (TRUS) prostate biopsies (PBx). As PCa treatment is only prescribed upon a positive diagnosis obtained through a prostate biopsy, PBx false negatives delay treatment or cure which, in turn, allows for localized cancer to potentially metastasize and spread to nerve bundles, affecting potency, and to bones, reducing cure or treatment options and worsening outcomes and quality of life for survivors, as seen in FIG. 5.

Some advanced techniques exist for prostate biopsies. Techniques such as fused PBx require an MRI to be performed on a patient approximately a week prior to a prostate biopsy. As may be appreciated, an MM requires the patient to pay radiologist fees to interpret the MM, perform another trip to a hospital, clinic, or medical imaging facility, and incur additional costs associated with the additional trip to the hospital or other medical facility. Moreover, a patient may lose wages from a missed day of work, may have difficulty arranging transportation from a rural area, and, more importantly, the trip or the MM may not be covered by various types of health insurance plans. Some payers refuse to reimburse biopsy-naïve patients for fused PBx requiring them to undergo a traditional biopsy first.

Accordingly, various embodiments are disclosed for a guidance and tracking system for templated or targeted biopsy and/or treatment and guided interventions. More specifically, a three-dimensional tracking, guidance, and visualization system for precision biopsy and precision treatment is described that can use prostate biopsy and radiofrequency (RF) ablation respectively in some embodiments. The embodiments described herein can work for various types of diagnosis: side-fire, end-fire TRUS PBx, transperineal PBx, and treatment, such as brachytherapy (steering and deposition of radioactive seeds next to lesions via a needle) and other guided interventions as can be appreciated.

In one embodiment, a guidance and tracking system may include a catheter having a tracking sensor, e.g., a six-degree-of-freedom (6-DOF) electromagnetic tracking sensor, such as the Model 90 from NDI or accelerometer/gyroscope arrangements, disposed therein, where the catheter may be adapted to be positioned and anchored in a body organ, preferably in an existing passage in the body or organ, such as the urethral passage in the prostate of a patient. Using tracking sensors, a tracking transmitter (e.g., NDI SRT or MRT), a tracking electronics unit (e.g., NDI DriveBAY), a computing device (e.g., a laptop such as a Microsoft Surface Pro), and other components described herein can be employed to track a location (x, y, z) and orientation (yaw, pitch, roll) of an organ and of a medical instrument during medical procedures, such as treatment or diagnostic procedures and guided interventions. The term "position" as used herein can refer to location and orientation. Similarly, a urethral catheter can include a urinary-catheter like tube placed in the urethra where the urethral catheter's cuff is intentionally inflated inside the prostatic urethra to anchor the catheter to the prostate, thereby tracking the prostate. The term "body sensor space", or in some embodiments "prostate sensor space" or "organ sensor space" can include a local coordinate system (for example, a coordinate system that allows tracking in six degrees of freedom) centered at the body sensor, prostate, organ, etc. as an origin.

Alternatively, the origin of a coordinate system could be at the tracking transmitter such as the NDI SRT transmitter. For the specific case of prostate biopsy, the term "body sensor space" can refer to a "prostate sensor space." The prostate sensor space can be preferable because the tracking transmitter can move (e.g., is accidentally bumped during the procedure) and the patient can also move. Using a prostate sensor space by using the prostate tracking sensor as the origin or reference point of the coordinate system renders the system robust and immune to patient or transmitter movement. The terms "systematic," "templated," or "random" biopsy are synonymous, relating to sampling an organ according to a template. Additionally, the computing device may determine a position of the medical instrument relative to the organ of interest. An echogenic liquid may be used in the catheter or the material of the catheter may be selected to be readily visualized when using medical imaging like ultrasonography or fluoroscopy such that the catheter is clearly visualized in a medical image that may prevent unintended sampling of the catheter or tracking sensor, during biopsy.

The guidance and tracking system may further include a graphical user interface (GUI) that incorporates, as part of a three-dimensional visualization tool, a rough segmentation feature configured to rapidly generate in quasi-real-time (e.g., about two minutes or less) a real, three-dimensional reconstruction of an organ, a lesion (e.g., a lesion within said organ), other associated features, as well as other three-dimensional objects. Internal passages that are visible in the imaging modality, such as the urethral passage of the prostate in TRUS, and other anatomical landmarks such as the bladder and seminal vesicles can also be reconstructed in three dimensions within the three-dimensionally reconstructed prostate. In experiments performed in accordance with the embodiments described herein, a three-dimensional reconstruction of the prostate was performed in less than two minutes, an achievement that ensures that the various embodiments of the system described herein can be streamlined and integrated without undue delay into the clinical workflow.

"Real three-dimensional" or "Real 3D" are terms used herein to refer to a three-dimensional environment that is truly three-dimensional, not merely one that gives the impression of being three-dimensional but is not, such as native 3D where the illusion of 3D via the "dimension" of depth is obtained by filming stereoscopically, i.e., where two cameras are used and positioned next to each other, thereby shooting at the same time to mimic each human eye. With a real 3D environment and real 3D visualization, an object, such as the prostate, is an actual 3D object within a 3D coordinate system and is correctly represented irrespective of the viewpoint (position) of a camera or an onlooker, i.e., whether the 3D object is viewed from the front, back, sides, top or bottom or any other perspective and also relative to other 3D objects, such as a TRUS probe, within the same 3D coordinate system.

In some embodiments, the three-dimensional reconstruction may be generated by manually tracing the outline or perimeter (discernible with the naked eye) of an organ for multiple two-dimensional (2D) images (slices) of the organ obtained using a transrectal ultrasound (TRUS) probe or other imaging technique. The manual tracing of the organ can be performed via a touch sensitive display, a mouse, trackball, pen, or other pointing or tracing device. In embodiments in which a templated (systematic) biopsy is being performed, the guidance and tracking system can superimpose a default 3D template that distributes the template locations or cores evenly around the 3D prostate or helps the user superimpose and adjust n (where n is 12 in a double sextant schema) template locations or cores on a customized, virtual 3D template on the three-dimensional reconstruction of the organ that may also comprise biopsy regions, regions of interest (ROI), or template locations or cores.

Figure 14:
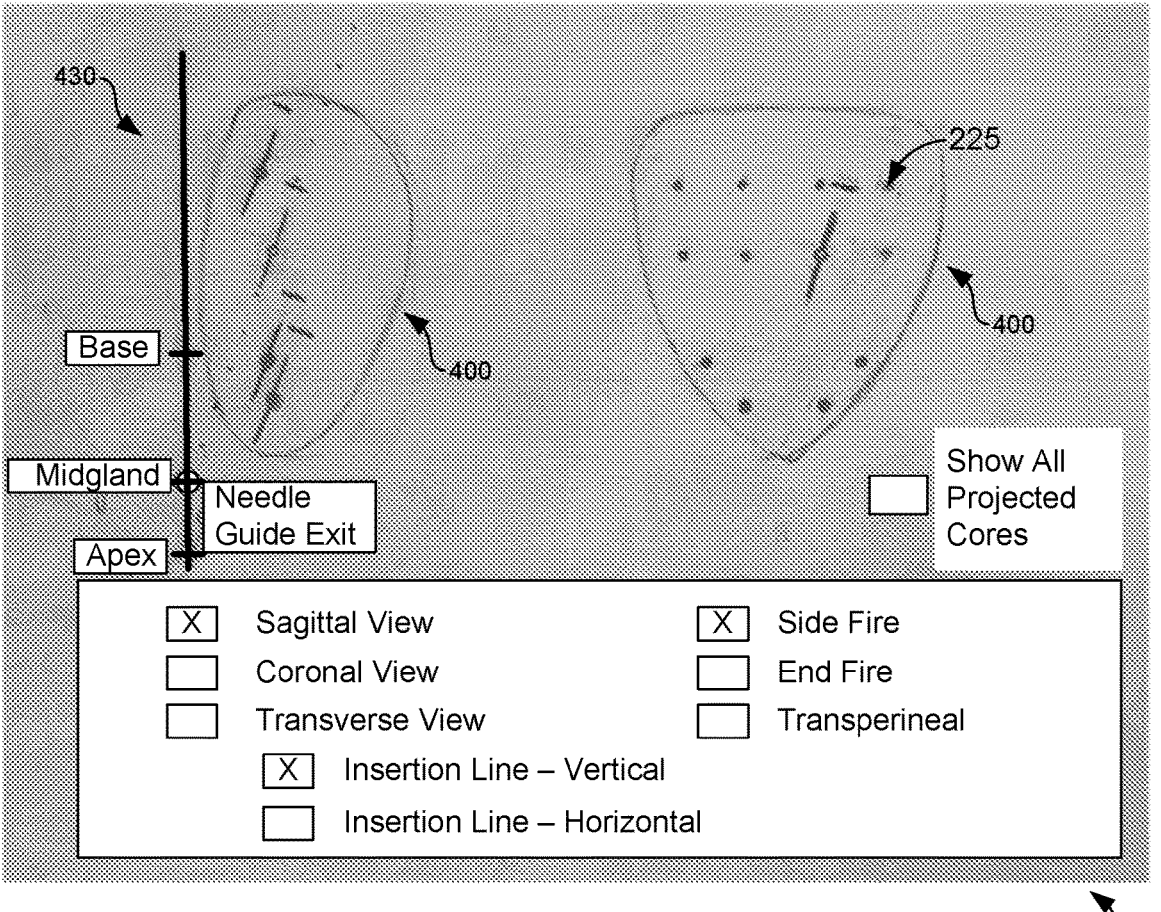
FIG. 14 includes an example of a user interface to create a user-adjustable template for pre-prostate biopsy planning that can be overlain in a user interface to facilitate proper adjustment of template or core locations a needle, probe, or other device in accordance with various embodiments of the present disclosure.

A virtual template can be placed relative to an organ shown in a display, where the virtual template can include ideal sites or locations and orientations for collection of tissue from the organ, as well as treatment sites in some embodiments. In some embodiments, the virtual template can include virtual cores representing elongated 3D shapes of actual cores (different core lengths, different core cross-sections, etc.) obtained with different types of biopsy needles (see FIG. 14).

Figure 15:
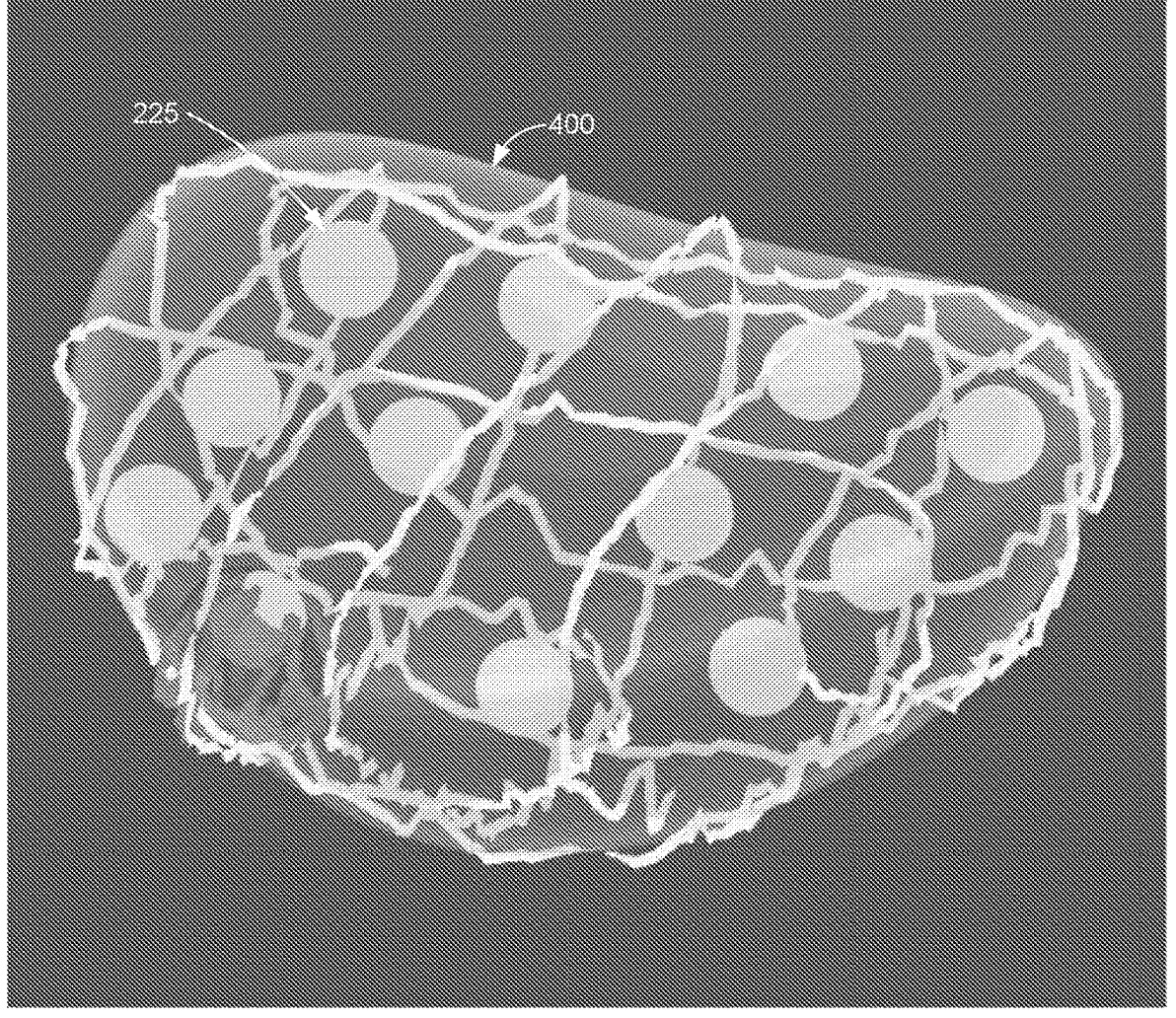
FIG. 15 illustrates traces in different planes for tracing an organ, such as a prostate, to create a real three-dimensional reconstruction of the organ, associated lesions, and anatomical features in accordance with various embodiments of the present disclosure.

The vertical bar to the left is a cognitive aid that is created during user adjustment of the template locations; it indicates the depth of insertion of the TRUS probe into the rectum with hash marks indicating where the needle guide exit (indicated by a circle) needs to be positioned to attain a desired template location in the user-adjustable template and can be used during actual biopsy. The hashmarks on the probe insertion depth line is back-calculated (as a template location is adjusted by the user) and displayed based on the known angle (e.g., 19o) between the side fire needle guide axis and the TRUS probe axis. The insertion depth line including the hashmarks created during the pre-planning adjustment and fitting of the template to the coarse-segmented prostate is then transferred to the FIG. 14 for use during the actual biopsy. Users can select different views for fitting the template to the prostate, including and 3D view (not shown in FIG. 15), sagittal, coronal and transverse.

The orientation of the cores can have a default orientation that matches the expected angle at which the needle will enter the prostate for a given side-fire needle guide or the angle of the needle guide to the TRUS probe longitudinal axis, e.g., 19° for the BK 8818 TRUS probe side-fire needle guide. Users can select a type and model of TRUS probe, type and model of needle guide, type, and model of biopsy instrument, and so forth such that the virtual core orientations and shapes are representative of the actual cores that will be obtained. The term "biopsy instrument" can refer to a biopsy needle with a handle, also known as a biopsy device, biopsy gun, or needle gun. The user-adjustable virtual cores on the adjustable sPBx template can also include an indicator, such as a red line (or other suitable indicator), indicating the maximum travel or excursion of the biopsy needle tip when it is fired. The indicator can be helpful in determining if the needle tip will go past the prostate boundaries and strike the bladder for example.

Figure 7:
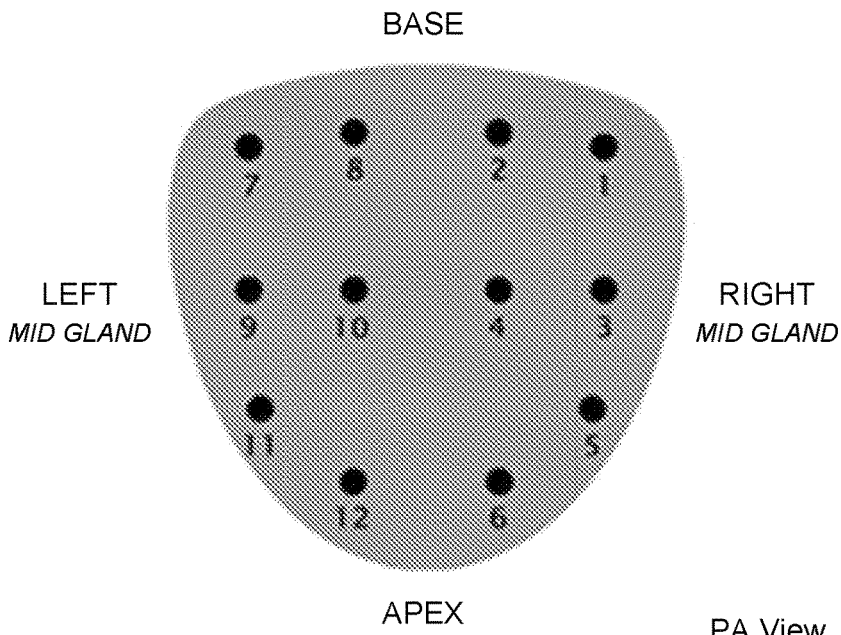
FIG. 7 is an example of a biopsy template, the commonly used double sextant schema and core sampling sequence, in accordance with various embodiments of the present disclosure.

Similarly, the red line or other indicator can indicate if the needle, when fired, will undesirably strike the urethra and users can then adjust the virtual core to avoid hitting the bladder, urethra, or other areas to be avoided. In situations where the user wants or needs to adjust the location or orientation of the cores in the template, such as when the template is too large for the prostate, the user can manually adjust the location and/or orientation of the template cores by clicking and dragging with a pointing device such as a mouse or selecting and dragging on a touch screen (see FIGS. 14 and 18). In situations where the user needs to add more cores to the template, such as when the prostate is too large for the template, additional cores can be created and placed by the user. The user may also choose the order of the template locations, i.e., the sequence in which the sample cores will be obtained (see FIG. 19). The user simply touches the cores in the desired sequence to establish in which sequence the cores will then be presented and highlighted for sampling during the actual biopsy procedure. The cores are numbered as shown in FIG. 19 in the sequence in which they were touched. Note that the sequence the user selected is different and more efficient in terms of time and motion than the standard sequence depicted in FIG. 7. As such, the proposed guidance and tracking system may provide guidance that facilitates the collection of samples in the locations specified in the template, including the anterior region of the prostate. The anterior prostate is currently knowingly not sampled during templated TRUS PBx, especially during side fire TRUS-guided transrectal PBx where the needle penetrates less anteriorly compared to end-fire TRUS PBx because the biopsy needle enters at an oblique angle to the rectal surface of the prostate with side-fire TRUS PBx. For instance, the guidance and tracking system described herein can provide trajectories and adjustments to the position (location and orientation) of a biopsy instrument or other medical instrument to facilitate collection of tissue samples in the areas specified in the virtual template or to provide treatment.

The actual biopsy needle can be visible in the TRUS image when inserted in the needle guide. When the needle gun is triggered, an inner biopsy needle with a half-cylinder recess cut into its side extends/springs out, e.g., by 22 mm, followed by, an outer biopsy needle that springs out to cut a roughly half-cylindrical 18 mm long core biopsy from the prostate. The biopsy needle is then removed from the patient to collect the biopsy. Sometimes, upon firing and springing forward, the needle tip ends up in the bladder (which may cause hematuria, blood in urine) because the user did not properly account for how far the inner needle tip extends, upon firing. To facilitate users visualizing and predicting where the core will be sampled, a virtual core (e.g., a thin line depicting a core 18 mm long and 1 mm wide, with the center of the core 8 mm away from the unfired tip of the needle as seen on the TRUS image) can be overlain on the TRUS image or imposed in an augmented reality or mixed reality environment, where the virtual core or other virtual template location is shown relative to an organ (see FIG. 3A).

For instance, a center of a virtual core can be visually displayed in the overlay in the TRUS image by an indicator, such as a circle in the middle of the core. The maximum excursion of the fired needle tip can be shown in the TRUS image by an indicator, such as a red line, 22 mm away or other suitable distance from the unfired needle tip. This visual aid facilitates users placing the center of the core at the intended prostate sampling location and realizing that the needle tip will pierce the bladder if the virtual core or maximum needle depth line impinges on the bladder in a mixed reality TRUS image (see FIG. 3A). Notably, the system described herein requires only a single imaging modality (ultrasound only; MM is not needed) and can be accomplished in a single patient visit.

An example of treatment using the system described herein is radiofrequency (RF) ablation, for example, of cancerous tumors, which is currently performed with fluoroscopy imaging (live x-ray) to position the needle inside the tumor. RF ablation for cancer is a minimally invasive procedure that uses electrical energy and heat to destroy cancer cells. The radiologist uses imaging tests to guide a thin needle through the skin or through an incision and into the cancerous tissue. High-frequency energy passes through the needle and causes the surrounding tissue to heat up, killing nearby cells. Because fluoroscopy uses x-rays, an ionizing radiation, there is concern about repeated irradiation of the hands of the clinician. Therefore, fluoroscopy guidance is intermittent with fluoroscopy turned off when the clinician is manually adjusting the needle to guide it to the target.

Figure 17:
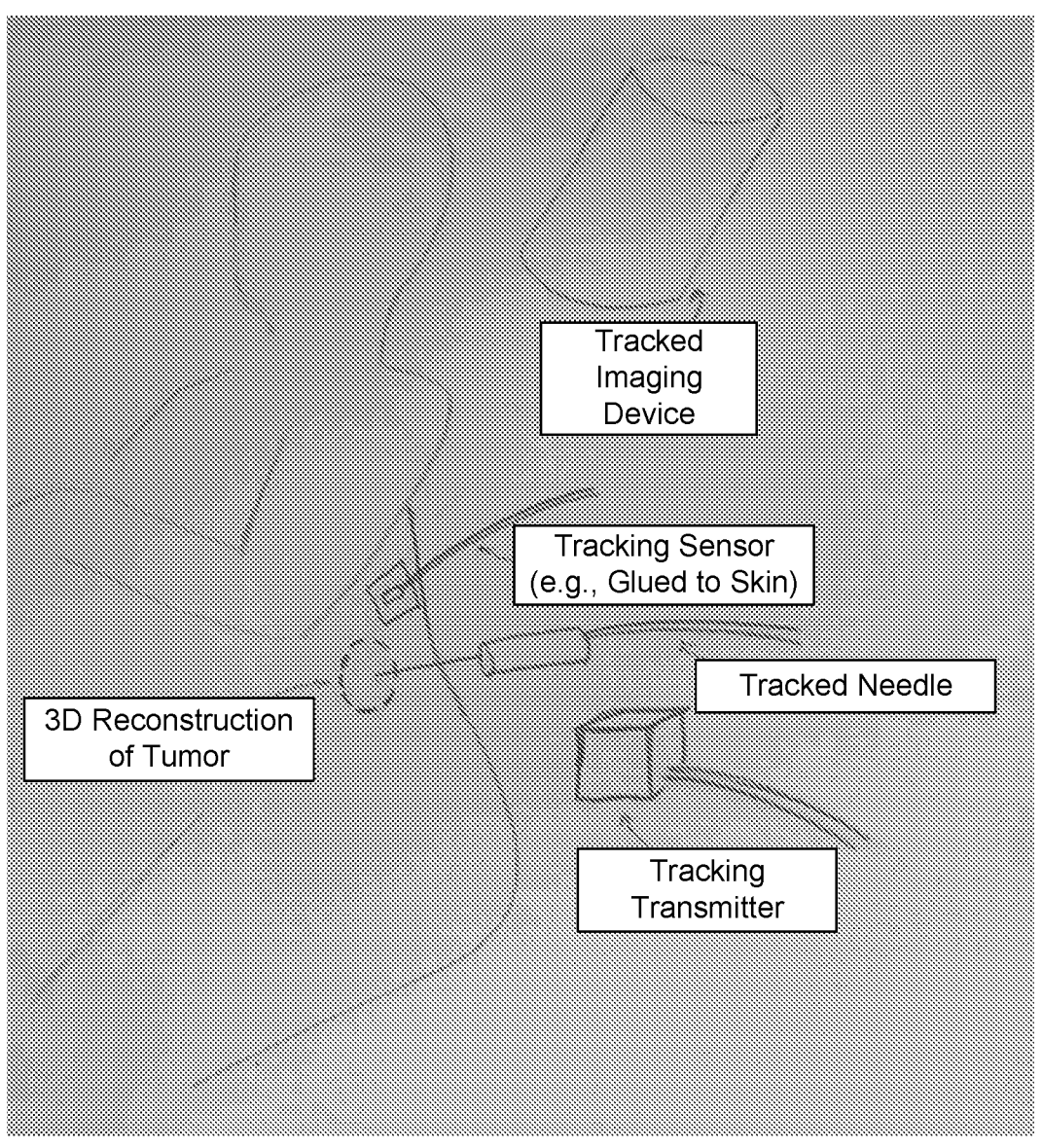
FIG. 17 illustrates a system for tracking a lesion, organ, or anatomical object using an external tracking sensor fixed to the skin or other accessible surface instead of an internal catheter for the purposes of guided intervention

Similar to tracing the outline (or perimeter) of the prostate on an ultrasound image at multiple slices or planes (e.g., 4-5 sagittal and 3 transverse), in the embodiments described herein, the outline or perimeter of a tumor or target space can be manually traced on a fluoroscopic image for the purpose of obtaining a real three-dimensional reconstruction of the tumor or target region. This is performed, for example, if the organ does not have an internal passage that can be used to place a sensor within the organ as we do using the urethral passage of the prostate. One or more tracking sensors attached to the patient (e.g., glued to the patient's skin with a sticky pad like an EKG electrode) can determine the coordinates of the tumor relative to the patient tracking sensor(s) and thus to a transmitter tracking the sensor(s) in preferably 6-DOF. Tracking the RF ablation needle or probe by attaching a sensor to the needle/probe or a needle/probe holder, allows the position of the RF needle tip or heating coil or probe to be determined relative to the tumor to be ablated. Another way of tracking a tool can include introducing a stylet inside a tool such as a needle whereby the stylet has a tracking sensor attached to it, ideally at the tip or at a relevant location such as the middle of a heating coil used for ablation. The transmitter tracks the location and orientation of the tracked probe, the tracked needle, tool, or stylet and the tumor via the tracking sensor attached to the patient's skin (see FIG. 17).

Once the initial fluoroscopic images have been obtained and the real three-dimensional reconstruction generated, fluoroscopy and its attendant risks of ionizing radiation to the clinician's hands and forearms can be turned off. Just like in the prostate biopsy application, the clinician can now use the virtual, reconstructed 3D tumor and the tracked needle within a real 3D graphical user interface (GUI) to guide a needle into the tumor in a real-time, real 3D visualization interface. Importantly, because there is no further need for fluoroscopy, the clinician does not need to continually stop as in the current art whenever the fluoroscopy machine is turned on to obtain an image. The clinician can work continuously and safely, using the mixed reality 3D tracking and guidance system to steer the RF ablation needle to the target. Observing and guiding the entire process in a real-time, real 3D visualization is also easier especially for spatially challenged clinicians compared to interpreting fluoroscopic images or two-dimensional images.

A notable gap when new devices are introduced is the omission of proper training to use the new device and techniques associated with the new device properly. Another design deficiency in devices is a non-intuitive user interface. Cognitive aids in the form of icons and other user interface elements provide assistance in processing information, location, orientation, and perspective that can help users quickly orient themselves and prevent mistakes as a result of users being disoriented.

Another gap in existing systems includes users being forced to perform mental rotations as well as other geometric and spatial mental manipulations because the orientation in the ultrasound image (including TRUS) of the object being scanned (such as a prostate) does not match the actual orientation of the physical object. For example, a prostate is shown in the sagittal TRUS image as if the patient is (a) lying supine and (b) as if the TRUS probe is sliding into the rectum from right to left when in actuality the patient is usually in the left lateral decubitus position (FIG. 9A).

Figures 9A, 9B:
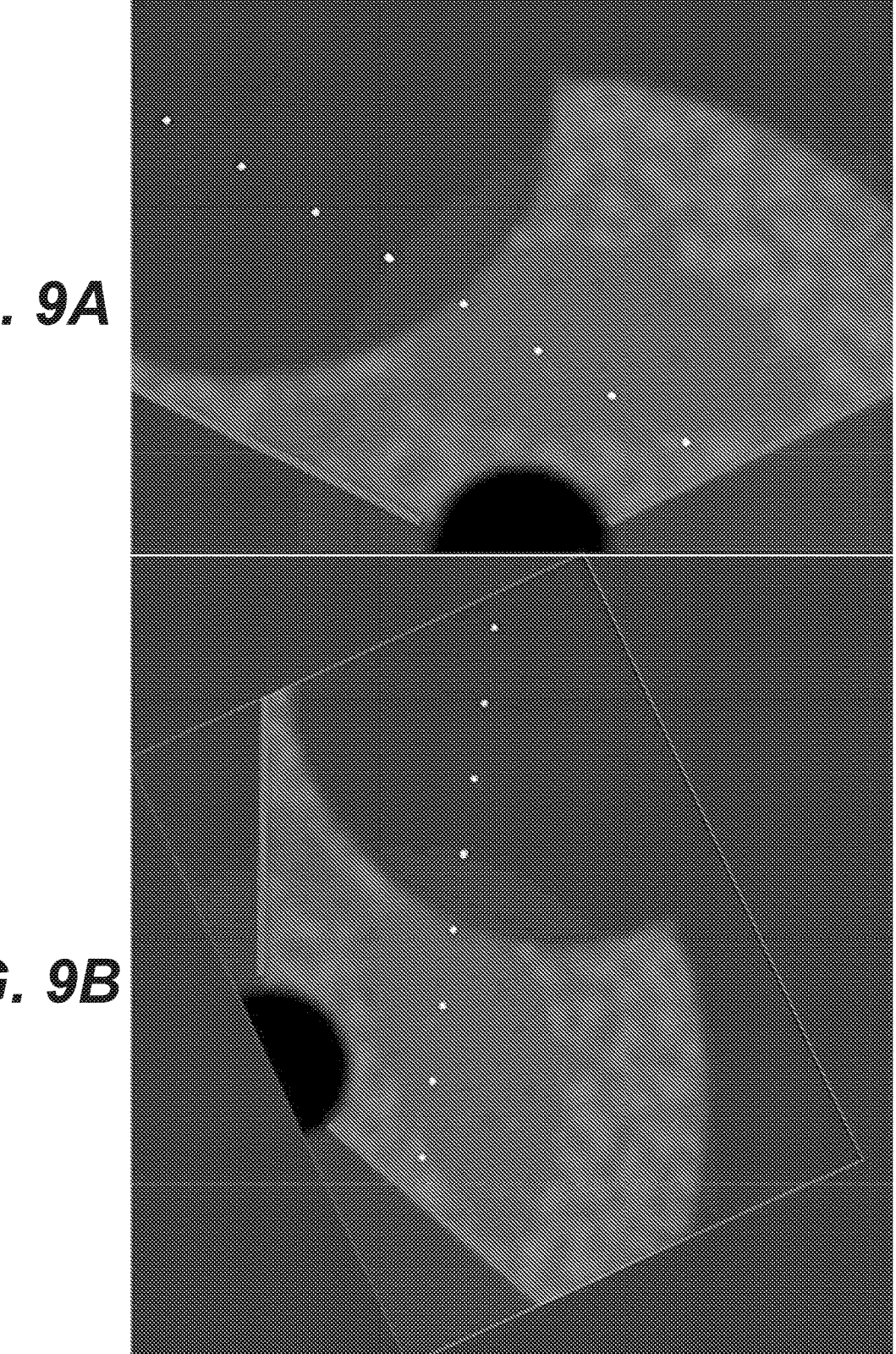
FIGS. 9A and 9B show a sagittal TRUS image that is not rotated (FIG. 9A) and the same TRUS image that has been rotated (FIG. 9B) so that the TRUS image is aligned with the insonation plane of the probe from the perspective of a user in accordance with various embodiments of the present disclosure.

Rotating the entire sagittal TRUS image so that the TRUS image aligns with the insonation plane of the probe from the user's perspective, i.e., about 90 degrees clockwise in the system reduces the need for mental rotation when interpreting the sagittal TRUS image and the TRUS probe movement (FIG. 9B). Similarly, the transverse TRUS image is currently displayed from a cephalad-caudad direction. Changing the viewing direction to caudad-cephalad as shown in the proposed orientation icon/cognitive aid, is more intuitive because the user is looking at the patient in a general caudad-cephalad direction.

Figure 10:
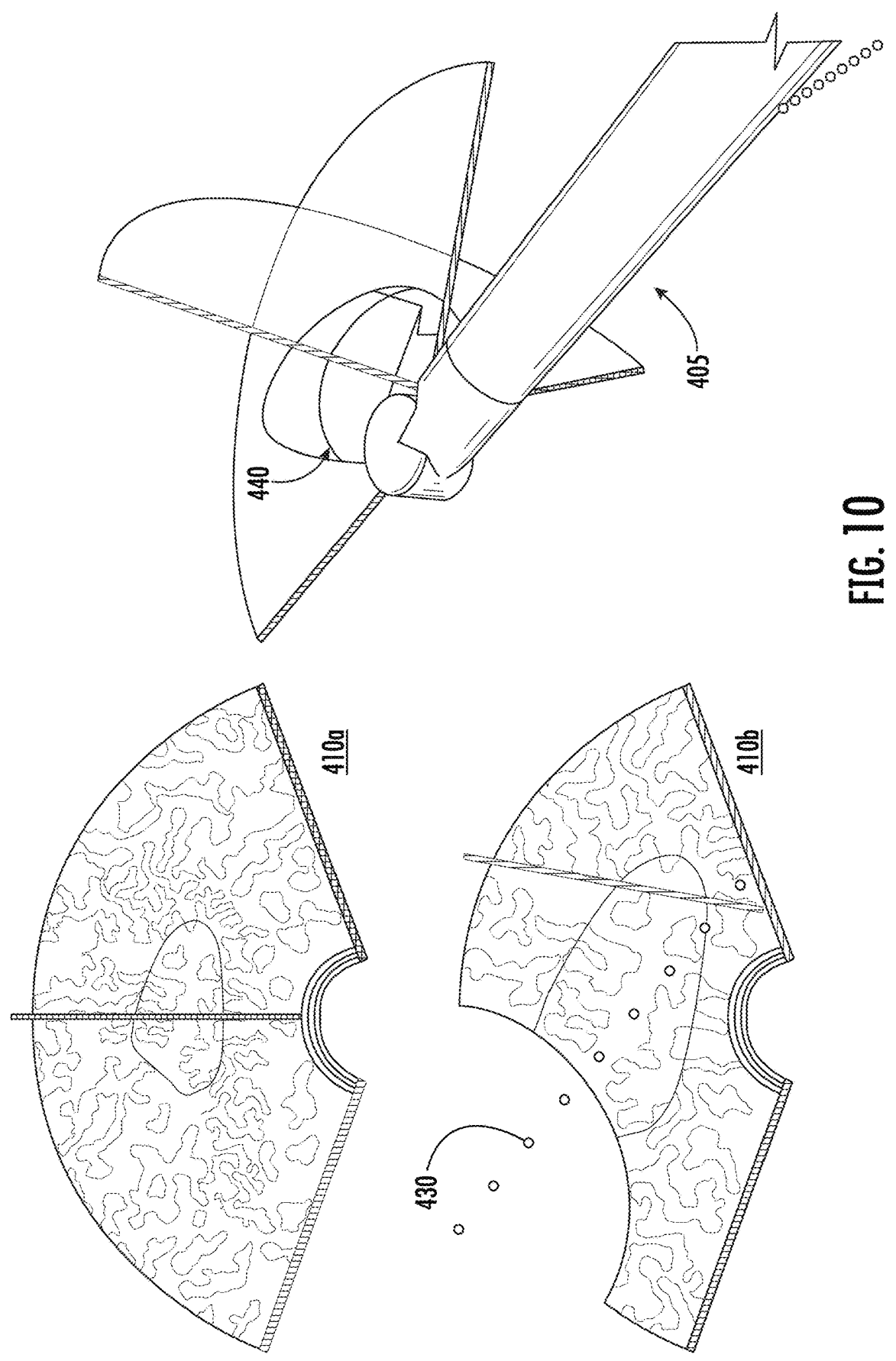
FIG. 10 shows a user interface with a three-dimensional visualization (perspective) rendered next to two views from a biplane TRUS probe (sagittal and inverse) in accordance with various embodiments of the present disclosure.

Yet another proposed embodiment for a user interface as described herein includes overlaying information on an actual TRUS image, such as TRUS images 410a and 410b to help orient users. For example, when using dual insonation planes during TRUS imaging, the edges of both insonation planes can be color coded and because the transverse and sagittal planes are orthogonal to each other, they would show as lines in each other's insonation planes. Each edge can have a unique color associated therewith. Each insonation plane can have two straight edges in the TRUS image. For example, given two TRUS insonation planes (sagittal and transverse), there can be four straight edges, each with a unique color. The edge-coloring scheme is used consistently in both the TRUS image and the 3D visualization 405 that depicts an organ 440. For purposes of illustration, FIG. 10 uses different line patterns to indicate the consistent edge-coloring scheme. In accordance with embodiments described herein, the line representing the edge of an insonation plane orthogonal to the insonation plane being displayed is color coded consistently helping to further orient users. Similarly, in the embodiments described herein, the intersection of the needle path dotted line in the sagittal TRUS image with the transverse insonation plane is represented as dots 430 in the transverse plane (see FIG. 10).

Figure 25:
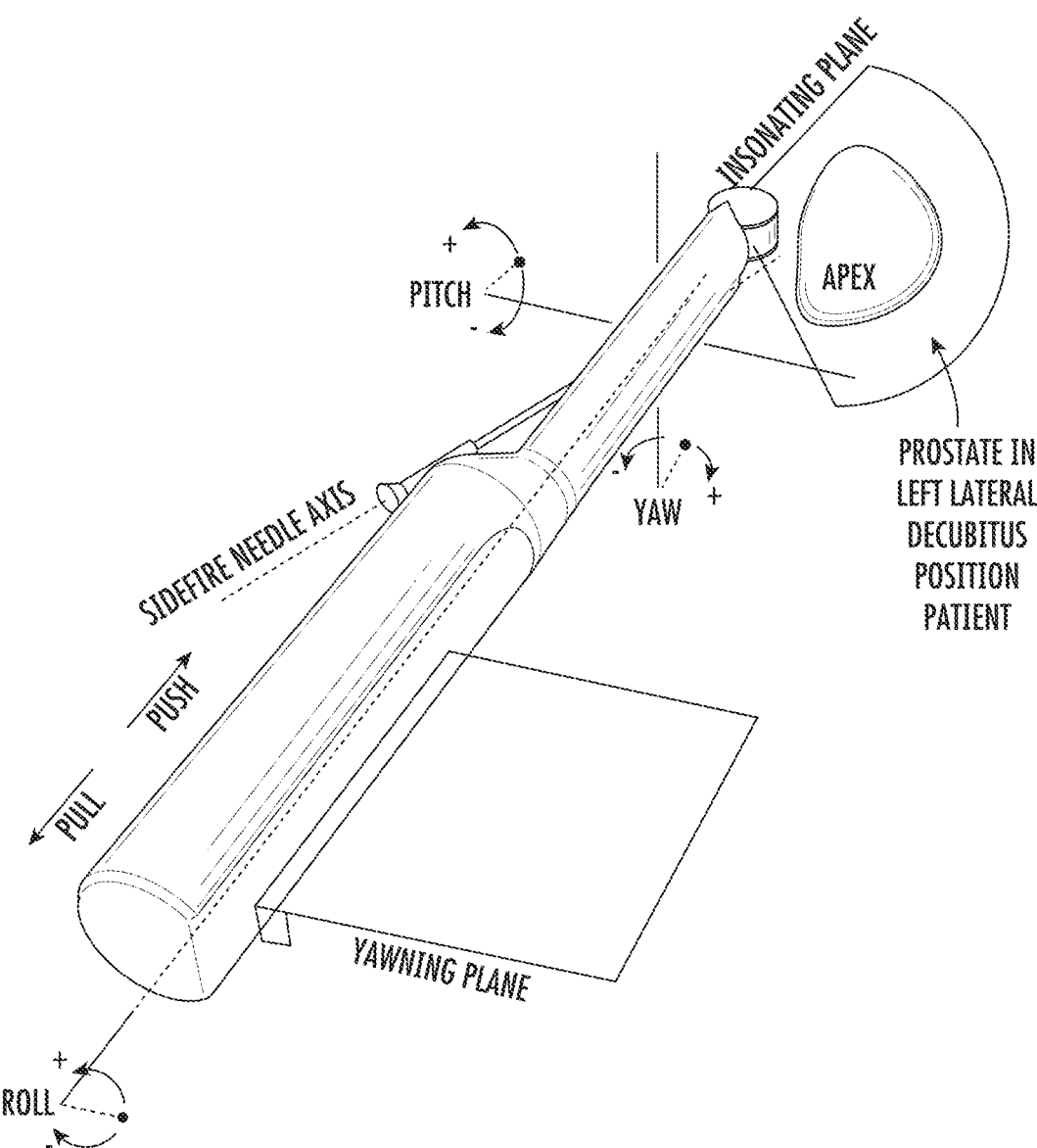
FIG. 25 shows the primary degrees of freedom of the TRUS biopsy probe in accordance with various embodiments of the present disclosure.

The pitch of a TRUS probe can be considered similar to an artificial horizon in an analogy to flight (see FIG. 25). If the pitch of the probe is not horizontal or neutral (distal tip of the TRUS probe is neither nose up or nose down when in neutral or horizontal position), there is less risk of users getting disoriented and taking all samples or biopsy cores in one half of the prostate instead of distributing them evenly and uniformly in both halves. It is difficult for users to judge whether the pitch is neutral and that is a common source of errors in evenly distributing cores to prevent the risk of false negatives. In the embodiments described herein, a small (29 mm long small block) air bubble water level ("bubble level") can be attached, for example, with self-adhesive to a TRUS probe handle to aid in keeping the pitch neutral. If the pitch is nose up, the bubble will float up and away from the user and if the pitch is nose down the bubble will also float up but closer to the user. The user is merely required to maintain the bubble in the middle to keep a neutral pitch. This bubble level can be applicable for both simulated and actual PBx. The bubble level can be integrated into the TRUS probe sensor clip 160b or into the TRUS probe 120.

Figure 13:
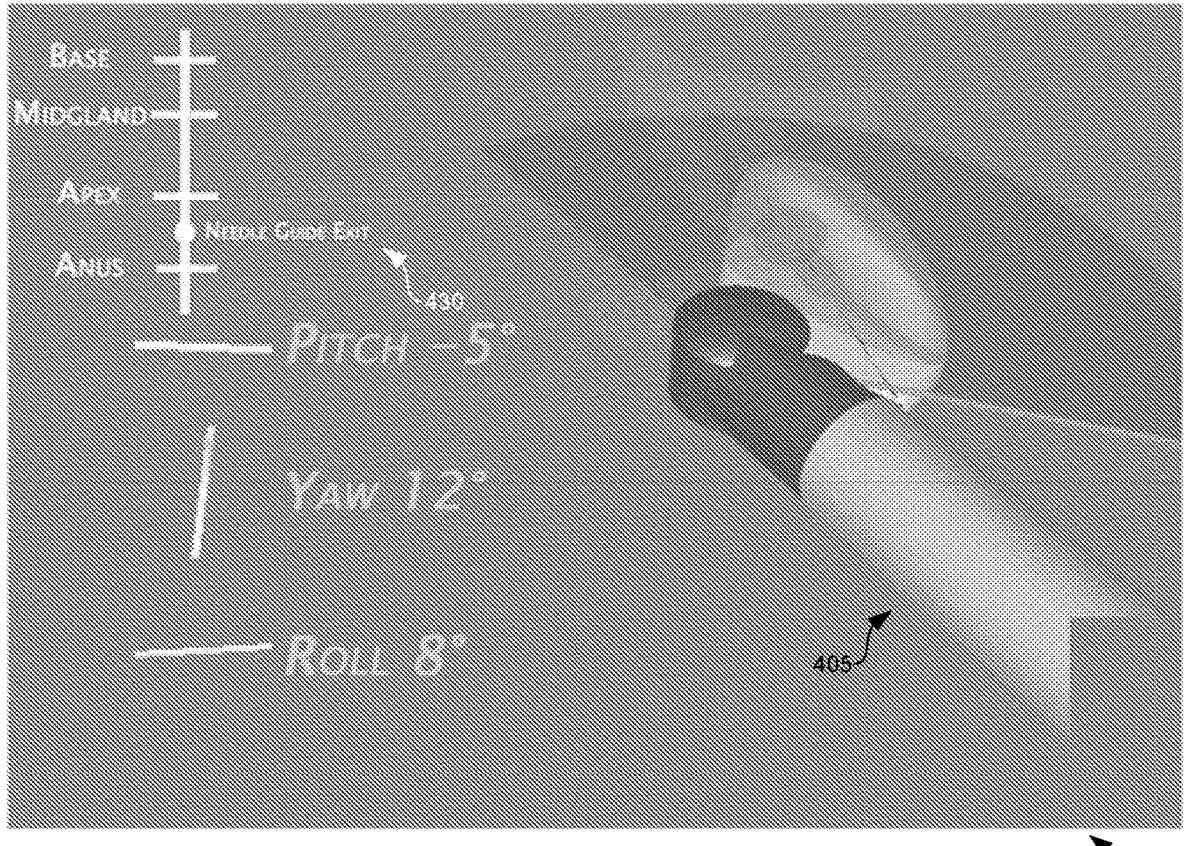
FIG. 13 shows a user interface that displays insertion depth, pitch, yaw, and roll as lines representing the amount of movement for each degree of freedom in accordance with various embodiments of the present disclosure.

In the case of a probe tracked with a 6-DOF sensor (for both patient care or use in a simulator), a line representing pitch can be used in addition to or instead of a physical bubble level previously described. In addition to the line representing the pitch of a tracked probe which is horizontal when the pitch is neutral and points up when the probe nose (distal tip) is up and down when the probe nose is down, other lines represent roll and yaw (see FIG. 13). Roll is when the TRUS probe is rotated about its longitudinal axis. A counterclockwise (CCW) roll to insonate the right prostate in a patient in left lateral decubitus is shown as an equivalent CCW rotation of the roll line indicator. In the neutral position, the roll line is horizontal, indicating no roll.

Figure 11:
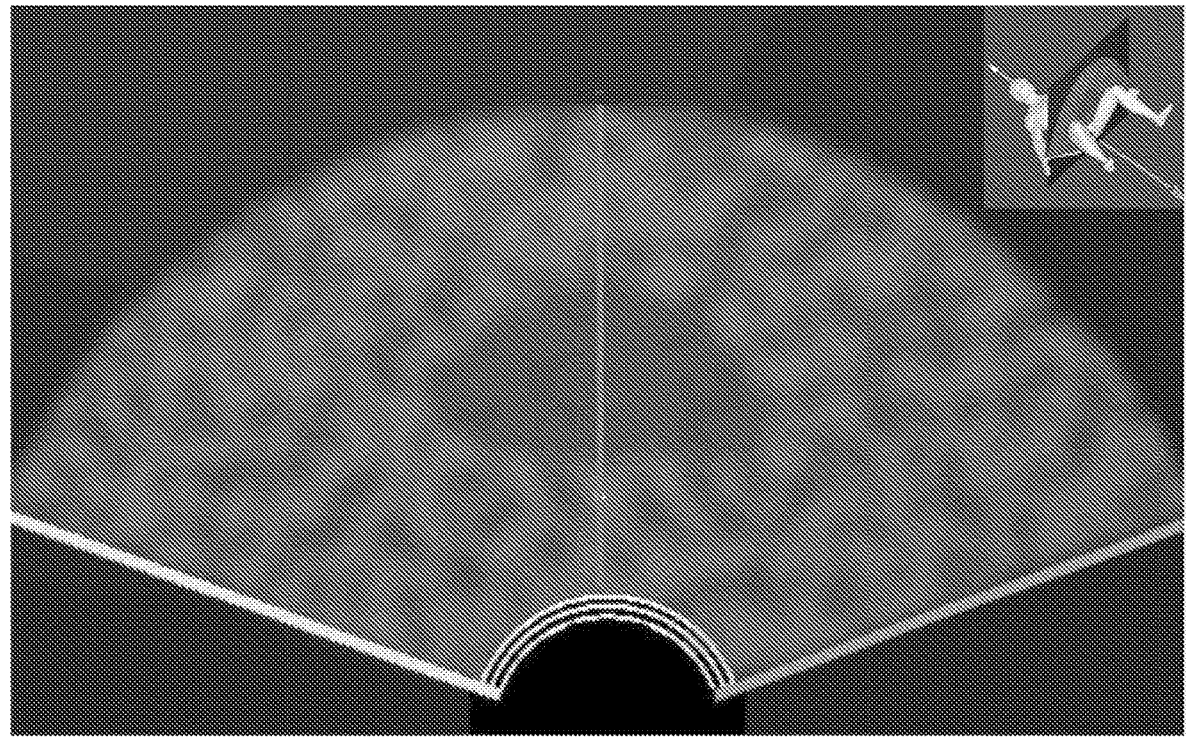
FIG. 11 include a user interface icon that shows an example body position (lithotomy) of a patient and the perspective from which to readily and intuitively interpret information for the displayed insonation plane in accordance with various embodiments of the present disclosure.
Figure 12:
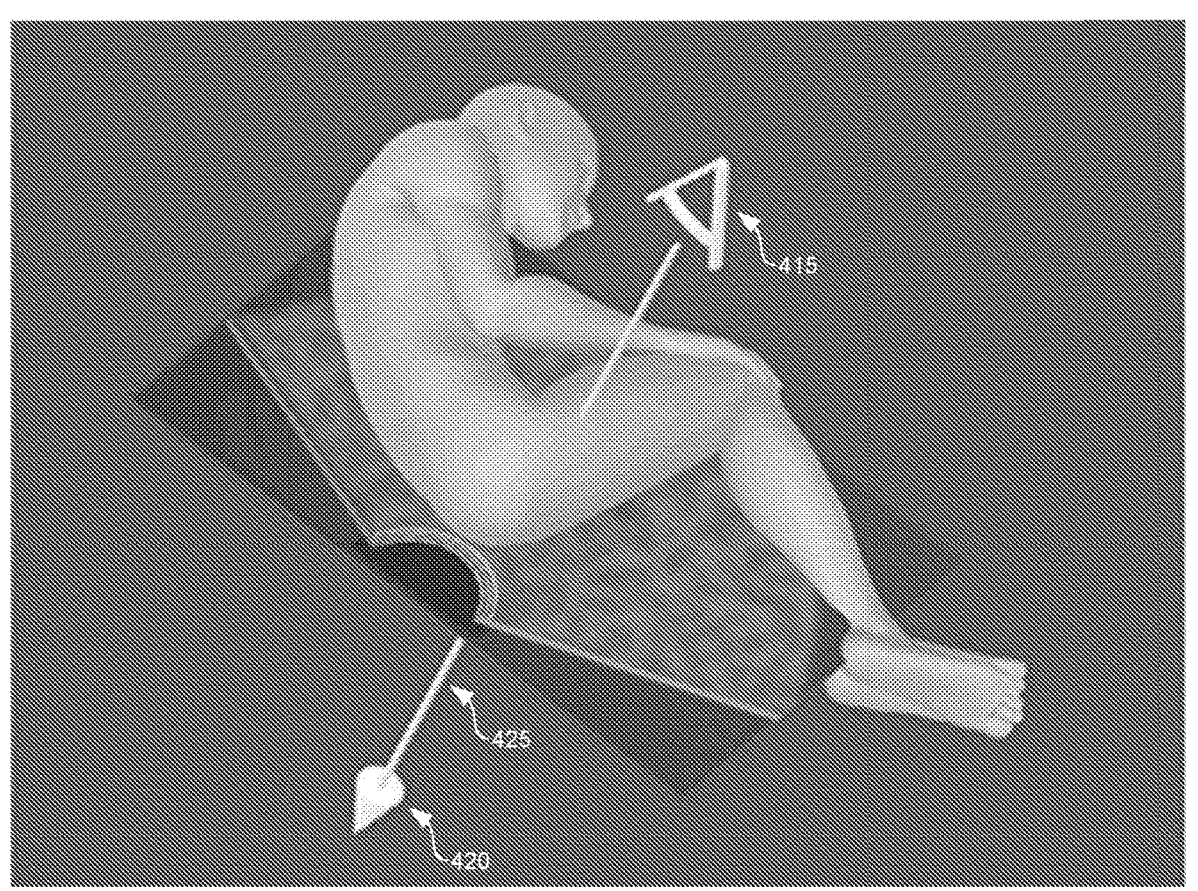
FIG. 12 shows another user interface icon that shows another example body position (left lateral decubitus) of a patient and the perspective from which to readily and intuitively interpret information from a given insonation plane in accordance with various embodiments of the present disclosure.

The degrees of freedom of the TRUS probe are shown in FIG. 25. Insertion depth (push-pull arrows) and roll are coarse adjustments, yaw is a fine adjustment. Pitch should be kept neutral (horizontal, 0°) if using the pitch-neutral technique. Other degrees of freedom are possible. The hashmarks on the probe insertion line determined during template fitting (FIG. 15) are used during the actual biopsy (FIG. 14) to readily determine how far to insert the probe. The needle guide exit moves relative to the probe insertion line as the probe is moved and the user stops the probe push or pull when the needle guide exit is at the hashmark for the intended template location. A hashmark can be made for each individual template location with the hashmark for the intended template location highlighted to being the only one displayed to minimize clutter In a further embodiment, the yaw line shows the lateral movement of the TRUS probe, i.e., whether the probe tip is being angled to the right or to the left. The yaw line is vertical for zero yaw. The upper tip of the vertical yaw line points right if the TRUS handle is moved to the left and vice versa. Further, there is a TRUS insertion depth line to indicate how far the TRUS probe is inserted. The depth line has hashmarks corresponding to the depth to insert the probe so that the needle exit hole on the needle guide is optimally located so that the needle trajectory when the needle is inserted in the needle guide is already aimed at a prostate region such as the base, mid-gland, or apex with minimal need for the use of yaw. The hashmarks on the insertion depth line can be created when the template or core locations are being adjusted in the template prior to the biopsy procedure. The numerical amount of pitch, roll, and yaw in degrees is also shown. Colors indicate if pitch, roll, or yaw is appropriate or inappropriate. For example, the pitch line and displayed number or text turns red when the TRUS probe pitch is too far away from zero (horizontal, zero pitch). The vertical bar at the top left is a cognitive aid that indicates the depth of insertion of the TRUS probe into the rectum with hash marks indicating where the needle guide exit (indicated by a circle) needs to be positioned to attain a desired template location in the user-adjustable template Users commonly ask from what perspective to interpret an ultrasound image that typically (3D ultrasound exists but is not commonly used) is a 2D cross-section of a 3D object(s). A dot or other suitable icon can be placed on a corner of an ultrasound image to correspond to a tactile physical marker on an ultrasound probe as an orientation marker. However, because different medical fields (e.g., cardiology vs anesthesiology) have the dots by convention in different locations (top right vs top left), manufacturers have accommodated these conventions by allowing users to choose where the orientation dot is located. This user-selectable mode can cause "mode confusion," and disorientation can occur if the dot is inadvertently left in the incorrect location for a given procedure. Furthermore, a 2D ultrasound image can be viewed orthogonally from two opposite sides. For example, a transverse view of the prostate in a TRUS image can be viewed with the observer at the head of the patient (cephalad to caudad direction) or from the feet of the patient (caudad to cephalad). In the embodiments described herein, intuitive icons can be employed that will inform users about where the insonation plane is located relative to the body and from what perspective the insonation plane is being viewed as in the attached figures as well as informing the user of the pose of the patient, especially if the patient is draped and not visible (FIGS. 11 and 12).

When viewing an image or slice, users often wonder from which direction the image should be viewed (e.g., head to toe? or toe to head?). The icons are examples of intuitive icons that readily orient the user to the right perspective. The icon in FIG. 11 shows the patient in the lithotomy position used for transperineal biopsy. The icons would represent the patient body in the lithotomy position or in other positions for other guided interventions. FIG. 11 indicates that the transverse view is caudad-cephalad, i.e., feet to head. FIG. 12 indicates that the sagittal view is left-right, i.e., read the image as if the user is at the left side of the patient and looking to the right side of the patient in a left lateral decubitus position. An icon 415 that looks like the letter A represents the eye. The direction of the perspective is reinforced by the arrowhead 420 at the other end of the viewing line 425.

The anterior zone of the prostate (region further from the rectum) is not currently sampled during systematic (templated) biopsy. Reasons for not doing so include the incidence of anterior zone lesions being small (while not zero), not warranting the risk of puncturing the bladder or urethra and the risk of creating more patient discomfort because the needle has to pre-penetrate the prostate before it is fired if the core is to reach the deeper anterior zone. According to various embodiments described herein, a method and cognitive aids can perform templated biopsy of the anterior zone in both actual and simulated TRUS PBx. A new template can be created for sampling at least 4 additional locations that are in the anterior zone as well as provide the ability for the user to actually drag and move the location of all templated positions through the GUI to account for the different sizes and shapes of prostates. In other words, users can add more template locations as needed to provide more coverage, including for a very large prostate.

When the needle tip is inserted and appears in the TRUS image, a dynamic cognitive aid can be placed in front of the tip of the needle as a line. In a biopsy needle such as the Bard MC1825 biopsy instrument, the needle tip springs forward when fired (e.g., by 22 mm) while the location of the center of a 18 mm core is roughly 8 mm from the needle tip. Cognitive aids, such as a small red line, may indicate where the tip of the needle will reach when fired. By ensuring that the red line is not in the bladder or urethra, guess work by having to eyeball or estimate distance is eliminated. If the red line does not touch the bladder, then bladder puncture will not occur. In other words, the user simply has to make sure the red line stays outside the bladder or urethra. Similarly, a yellow line indicates the predicted biopsy core and a yellow dot indicates where the center of the biopsy core will be on the line denoting the predicted biopsy core. Users can then line up the yellow dot so it coincides with the black circle/sphere (e.g., 2.5 mm diameter indicating the template location) in the middle of the green circle/sphere (e.g., 5 mm radius, indicating the acceptable deviation) to get the center of the biopsy core as close to the templated location as possible. This feature would be adapted for different core lengths and sizes and is used both in the TRUS image overlay and in the 3D visualization.

Figure 1:
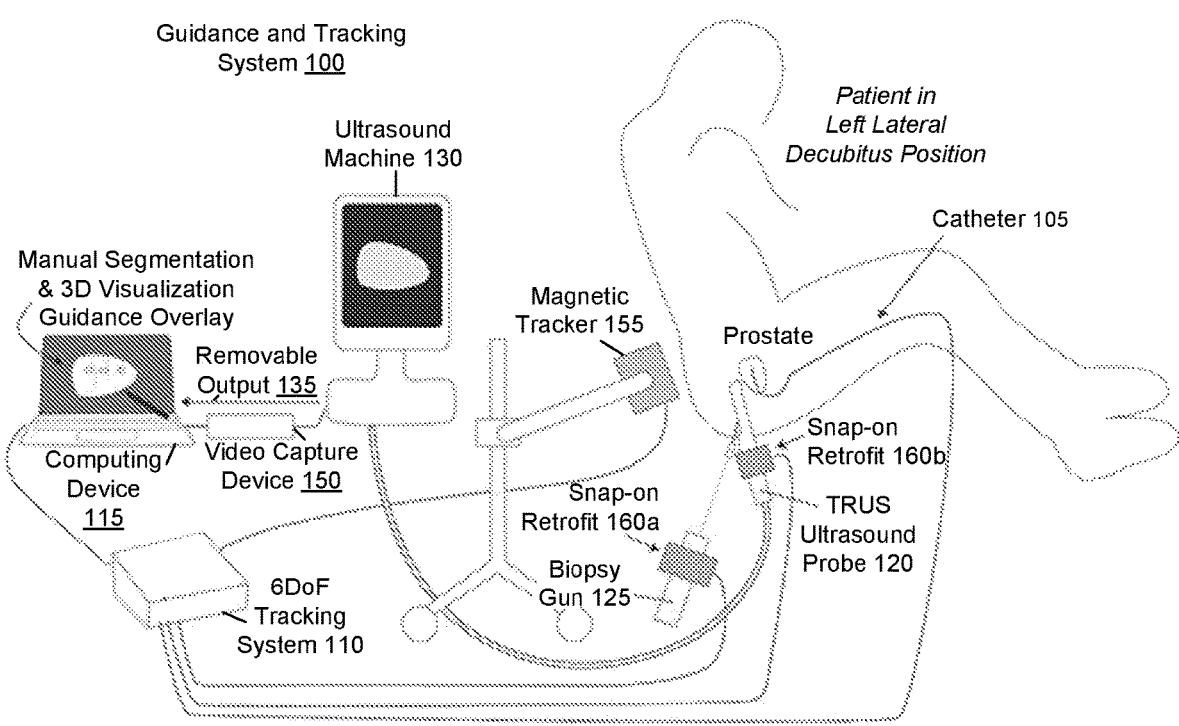
FIG. 1 is a system diagram of an example of a guidance and tracking system for templated and targeted biopsy and/or treatment in accordance with various embodiments of the present disclosure.

Referring now to FIG. 1, a guidance and tracking system 100 (also referred to as a TRUS patient care system) may include a catheter 105 and a six-degree-of-freedom (6-DOF) tracking system 110 for tracking a tracking sensor (e.g., NDI model 90) disposed in the catheter 105. As the catheter 105 can be tracked by the 6-DOF tracking system 110, the catheter 105 can be referred to as a tracked catheter in some embodiments. The catheter 105 can be configured to be positioned and anchored in the urethral passage of the prostate in some examples. Using an electromagnetic tracking sensor positioned in the catheter 105, a computing device 115 can to track a location and orientation of an organ, such as the prostate as shown in FIG. 1, although other organs can be tracked according to various embodiments described herein. While FIG. 1 is specific to the retrofit embodiment, another embodiment (not retrofit, but inbuilt) can include embedding tracking sensors 160*a* and 160*b* into respective tools and imposing overlays on a TRUS machine 130 display, and the computing device 115 and its associated software can be all or a portion of the TRUS machine 130.

The computing device 115 of the guidance tracking system 100 can include a tablet, smartphone, laptop, or similar personal computing device having a touch screen or stylus-enabled display in some embodiments. In further embodiments, the computing device 115 can include a server. By attaching or embedding a tracking sensor to a medical instrument, such as a TRUS ultrasound probe 120 (or TRUS tracking clip 160*b*) and/or a biopsy gun 125 (or biopsy device clip 160*a*), the medical instrument can be tracked during a treatment or a diagnostic procedure using a tracking application 215 (FIG. 2), a guidance application 220 (FIG. 2), or other application. In some embodiments, the biopsy gun 125 includes a spring-loaded biopsy needle (e.g., a Tru-Cut biopsy needle) that may be additionally tracked by another electromagnetic sensor.

The location and orientation of the prostate tracking sensor, the TRUS probe tracking sensor 540, and the needle gun tracking sensors 530 can be detected by a magnetic tracker (transmitter) 155, such as an NDI SRT (Short Range Transmitter) or MRT (Medium Range Transmitter) tracker (transmitter) located, e.g., above the right hip with the patient in a left lateral decubitus position, such that the transmitter's tracking volume encompasses the expected and clinically relevant range of movement of the organ and of the instrument. Additionally, the computing device 115 may determine a position and orientation of the one or more medical instrument relative to the tracked organ. The medical instrument can include the biopsy gun 125 for biopsy or a RF needle for ablation treatment.

In various embodiments, an echogenic liquid may be used in the catheter 105 or in the material of the catheter such that the catheter 105 is clearly visualized in an ultrasound image, shown on a display of the computing device 115, which may prevent unintended sampling of the catheter or electromagnetic tracking sensor.

Further, the guidance and tracking system 100 may include an ultrasound machine 130, a removable output 135 (e.g., a removable HDMI output), a video capture device 150, a magnetic tracker 155, as well as one or more snap-on retrofits 160*a*, 160*b*. The computing device 115 can be configured to provide a manual segmentation to generate a three-dimensional reconstruction (e.g., a real three-dimensional model) of an organ, such as the prostate that can be used in a three-dimensional visualization guidance overlay, as will be described.

Figure 24:
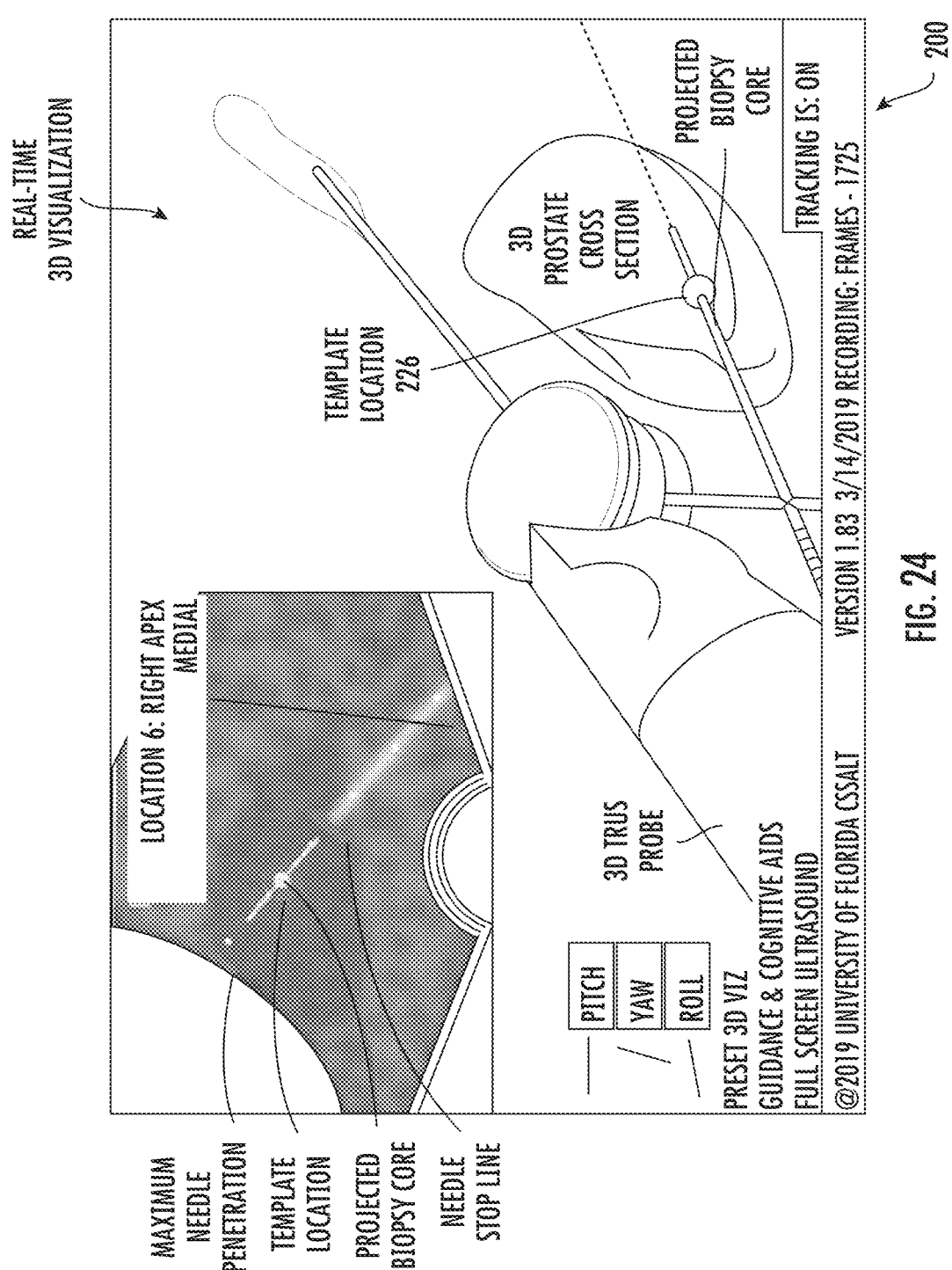
FIG. 24 shows the user interface of a proposed embodiment with some cognitive aids enabled, in accordance with various embodiments of the present disclosure.

Additionally, various user interface components can be shown in association with the organ and/or three-dimensional reconstructions of the organ that facilitate a medical procedure, such as a biopsy of the prostate (FIG. 24). In one embodiment, a core template is shown visually overlain on a live view or a three-dimensional reconstruction of an organ that guides proper placement of a predicted biopsy core to the intended core in the template. For instance, the computing device 115 can generate notifications that assist the operator in moving the biopsy gun 125 to match the predicted core to the intended core in the template such that an ideal and proper biopsy can be performed with minimal deviation. Cognitive aids include the projected biopsy core intersecting a template location in a cross section of the prostate in the 3D visualization, and TRUS image overlays such as template location, needle stop line, maximum needle tip penetration line, biopsy core center, and projected biopsy.

Figure 2:
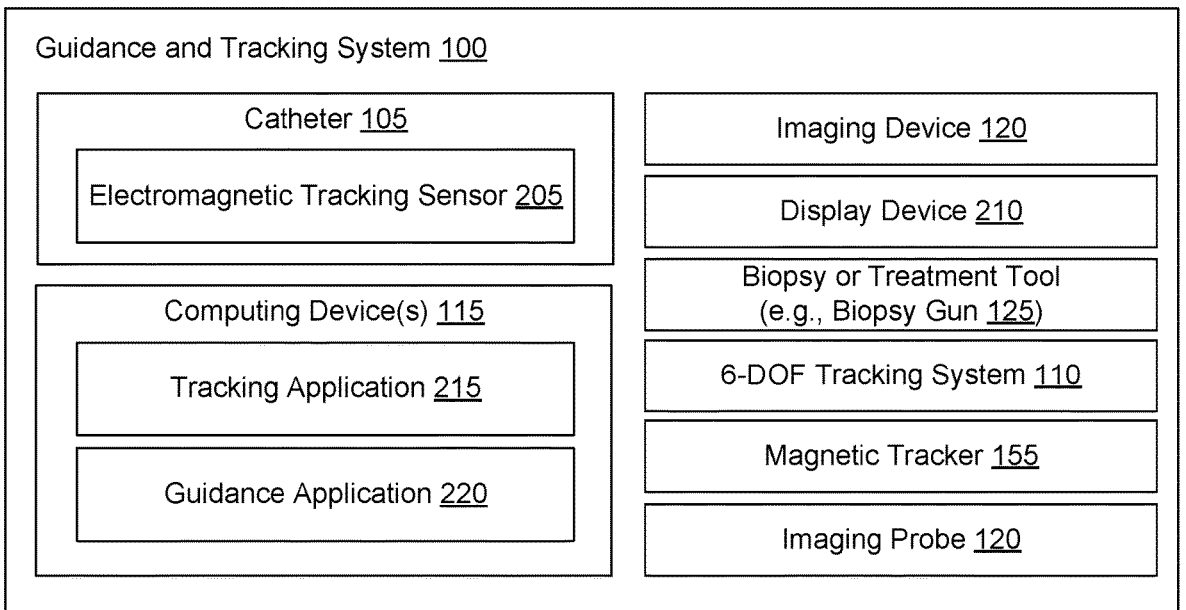
FIG. 2 is a schematic diagram of an example of a guidance and tracking system for templated and targeted biopsy and/or treatment in accordance with various embodiments of the present disclosure.

Similarly, by attaching or embedding a tracking sensor to a medical instrument (e.g., a 6-DOF electromagnetic sensor to a TRUS probe 120 with or without a biopsy needle guide), the medical instrument can be tracked during a treatment, diagnostic, or guided intervention procedure using a tracking application 215, a guidance application 220, or other application, as shown in FIG. 2. However, referring back to FIG. 1, a biopsy gun 125 or other type of needle gun that includes a spring-loaded biopsy needle (e.g., a Bard Tru-Cut biopsy needle) may be additionally tracked by another electromagnetic sensor. The location and orientation of the prostate tracking sensor and of the TRUS probe and needle gun tracking sensors can be tracked by a transmitter, such as an NDI SRT (Short Range Transmitter) or MRT (Medium Range Transmitter). In some embodiments, the transmitter can be located, for example, above the right hip with the patient in a left lateral decubitus position, such that the transmitter's tracking volume encompasses the expected and clinically relevant range of movement of the organ and of the instruments. Additionally, the computing device 115 together with the application 215 can determine a location and orientation of one or more medical instruments relative to the tracked organ.

The medical instrument can include an imaging device, a biopsy needle gun for biopsy, a RF needle for ablation treatment, or any other guided intervention tool. In various embodiments, an echogenic liquid may be used in the catheter 105 or in the material of the catheter such that the catheter 105 is clearly visualized in an ultrasound image or other medical imaging modality, which can prevent unintended sampling of the catheter or electromagnetic tracking sensor.

The embodiments differ from the prior art in multiple ways. Among many differences, embodiments of the present disclosure (a) do not necessarily require two imaging modalities (e.g., MRI and ultrasound), but can include previously obtained imaging data from other imaging modalities, if desired (i.e., the techniques described herein do not require a fused biopsy technique that fuses images from two different sources); (b) do not require an enhanced catheter device to be present during the "first imaging modality", e.g., MRI imaging; (c) do not require "image space" and the need to collocate "image space" to "patient space"; (d) do not require any imaging modality at all, such as TRUS, once the templated locations or cores or reconstructed visible lesions have been 3D reconstructed and registered; and (e) do not require the sensor in the catheter to be visible in the image space, i.e., visible with MRI imaging. Rather, the location and orientation of the organ tracking sensor is determined by a transmitter that tracks the sensor. In some embodiments, the transmitter can be located outside the patient's body and can be configured to track, in six degrees of freedom (x, y, z, yaw, pitch, and roll) for example, the sensor in the catheter. Thereby, the sensor can then be precisely collocated onto the TRUS image or other image and overlaid as a virtual sensor onto the TRUS or other image. In the embodiments described herein, the user has the option to work in a three-dimensional visualization mode instead of having to rely on a two-dimensional TRUS image and the user's spatial ability in shifting from a 2D frame to a 3D frame.

As a consequence, the embodiments described herein are more streamlined and affordable by eliminating the costs and time of an MRI and the radiologist fees for interpreting an MRI as existing fused biopsy systems known in the prior art. The embodiments described herein are also more intuitive to use, even for users with limited spatial ability or cross-sectional literacy (ability to mentally visualize a 3D object from a 2D cross-section); a TRUS image is a 2D cross-section or slice of a 3D organ, such as the prostate. The embodiments described herein provide a more intuitive user interface than the current PBx art as it provides a real-time 3D visualization as a real 3D graphical user interface that can compensate for lack of spatial ability and cross-sectional literacy and the limitations of 2D TRUS imaging.

The medical instrument(s) can include an imaging device, such as a transrectal ultrasound probe or other imaging device 135. Further, the medical instrument(s) can include a biopsy, or guided intervention treatment device, which may include a biopsy needle gun for collecting samples, or other device for providing therapeutic treatment. The medical instrument(s) may include a sensor (inbuilt or removably attached) in some embodiments for tracking the medical instrument. The computing device 115 can interact with a display device 210 (FIG. 2) to generate a user interface that can also be a guidance interface, as will be described.

Referring now to FIG. 2, a schematic diagram of the guidance and tracking system 100 is shown in accordance with various embodiments. Again, the guidance and tracking system 100 can include a catheter 105 having an electromagnetic tracking sensor 205 positioned therein in some embodiments. The guidance and tracking system 100 can include a display device 210, such as a computer monitor or a touch screen display device, which can be a part of or separate from the computing device 115 in some examples. The computing device 115 can include program instructions that facilitate the tracking and collection of data regarding the catheter 105 as well as an organ, such as the prostate. As such, the computing device 115 can include a tracking application 215, a guidance application 220, as well as other applications, services, engines, or other computer-implemented program instructions.

The medical instrument(s) of the guidance and tracking system 100 can include an imaging device, such as a TRUS probe 120 or other imaging device. Further, the medical instrument(s) can include a collection or treatment device, which can include a biopsy needle gun 125 for collecting samples, or a device for providing therapeutic treatment. The medical instrument(s) can include a sensor in some embodiments for tracking the medical instrument. The computing device 115 may interact with a display device 210 to generate a user interface, as will be described.

Figure 3A:
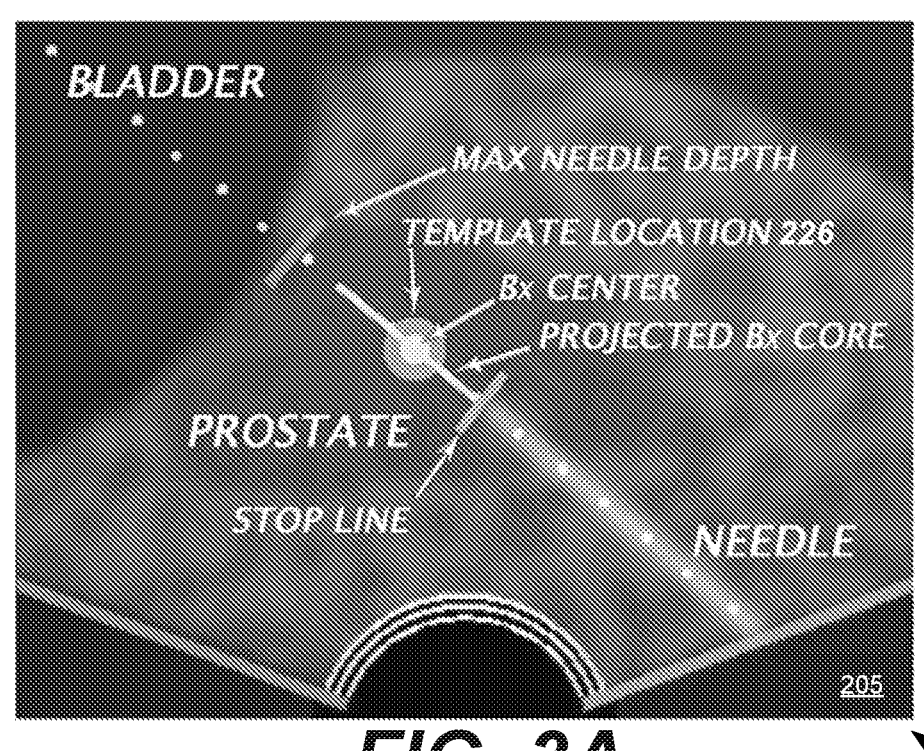
FIG. 3A is an example of a mixed reality graphical user interface that includes a TRUS image and an overlay of registered, virtual cognitive aids designed to augment the TRUS image and facilitate accurate biopsy.
Figure 8:
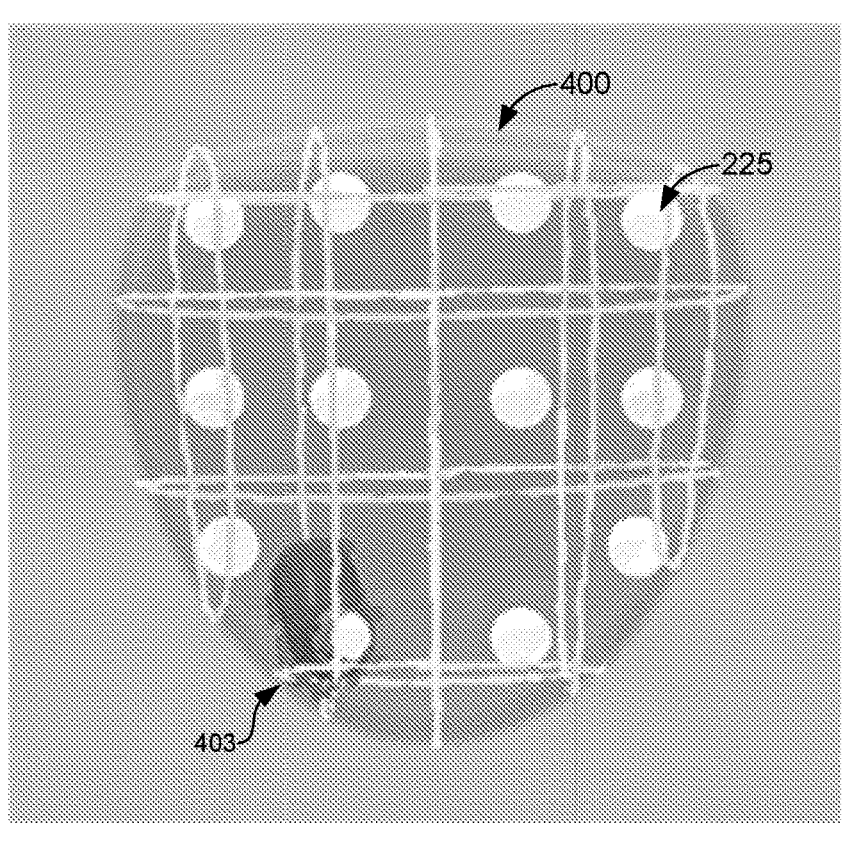
FIG. 8 illustrates tracing an organ, such as a prostate, to create a three-dimensional reconstruction of the organ and an associated lesion in accordance with various embodiments of the present disclosure.

Moving on to FIG. 3A, an example of a user interface 200 is shown, where the user interface 200 includes an ultrasound image 205. As noted above, the guidance and tracking system 100 can include an imaging device configured to capture multiple images of an organ that can be used to generate a three-dimensional reconstruction (segmentation) of an organ. In some embodiments, a three-dimensional reconstruction 400 (FIG. 6) can be generated based on multiple two-dimensional images of the organ obtained using a TRUS probe 120 or other imaging technique. In instances where a lesion or a region of interest is visible in the TRUS image (i.e., the lesion is visible with ultrasound imaging), the outlines of the lesion at different two-dimensional slices can be manually traced to form a three-dimensional reconstruction of the lesion 403, where an example of the process is shown in FIG. 8. The three-dimensionally reconstructed lesion 403 can then be targeted during biopsy, i.e., the guidance and tracking system 100 can be used for targeted biopsy, in addition to templated biopsy.

The circle of FIG. 3A indicates a template location. The stop line or needle stop line is a visual cognitive aid overlay to indicate how far the needle tip needs to be inserted before it is fired so that the white center of the cylindrical biopsy core is at the center of the gray circle. The stop line, shown in FIG. 3A, is not present if the needle is not properly aligned to the intended location or target. The vanishing stop line serves double duty as a reminder that the aim of the needle is off from where it needs to be. In some embodiments, the stop line appears gray when the needle is somewhat aligned to the intended location or target. Further, the stop line can turn green when the needle is properly aligned to the intended location or target. The projected half-cylindrical biopsy core and a dot representing the biopsy core center also overlay the live ultrasound image. A line (e.g., a red line) can represent the maximum excursion (depth) that the tip of the biopsy needle device will reach when fired is also shown. The maximum needle depth line may change color and/or flash to alert the user that the needle, if fired, will damage anatomical structures behind the prostate. The maximum needle tip excursion line and the projected biopsy core and center dot move together in real time along the needle path as the tracked needle is inserted past the needle guide.

The template 225 is a series of template locations, e.g., 12 in a double sextant schema. In embodiments in which a biopsy of a prostate or other organ is being performed, the guidance and tracking system 100 can superimpose a virtual template 225 on the three-dimensional reconstruction 400 of the organ, as shown in FIG. 8. Referring back to FIG. 3A, notably, the virtual template 225 can include template locations or ideal sites for collection of tissue from the organ or for treatment. Alternatively, only one template location 226 or core can be displayed at a time within the ultrasound image, as shown in FIG. 3A, to reduce visual clutter and facilitate the user focusing on the location being sampled.

As such, the guidance and tracking system 100 can provide guidance that facilitates the collection of samples in the locations specified in the virtual template 225. The current mental model for 12-core templates in urology training materials is a qualitative 2D model that seems to ignore that the prostate is a 3D, not a 2D organ. In other words, the current 12-core template does not specify how anteriorly the circles (or spheres) depicting the suggested template locations in a given template are located. The embodiments described herein allow placing the template locations in a quantitative 3D, instead of a qualitative 2D, biopsy template, including anteriorly and guiding the biopsy needle to that template location.

Further, a current technique that is taught for side-fire templated biopsy is to insert the needle until, in the TRUS image, the needle tip is observed to tent the prostate capsule on the rectal side of the prostate and fire the needle gun. This capsule-tenting technique does not pre-penetrate the prostate and will not sample the anterior region of the prostate where lesions do occur, especially with a side-fire needle guide. In other words, the current art for templated biopsy will knowingly not sample the anterior prostate and will therefore miss an existing anterior lesion, leading to a false negative. Reasons that have been advanced for systematically not sampling the anterior prostate include concern about inadvertently striking the bladder or urethra with the biopsy needle. The embodiments described herein allow placing template locations in the anterior region of the prostate and collecting samples at those locations while avoiding the bladder and urethra.

In various embodiments, the virtual template 225 can include a twelve-core template although, in other embodiments, other suitable amount of cores or other template schemas including transrectal and transperineal template schemas may be employed. The embodiments described herein facilitate the creation of standard or customized 3D templates that sample the anterior region of the prostate during side fire transrectal, end-fire transrectal and transperineal templated TRUS-guided PBx and provides guidance about the proper amount of pre-penetration into the prostate by the needle tip prior to firing the needle gun. Further, if the selected, pre-configured template does not fit the prostate of the patient or cover an area that the user wants to sample, the user has the ability to manually and visually adjust the location and orientation of the template locations or cores to obtain a better fit or coverage between the reconstructed 3D prostate and the template. Additionally, in various embodiments, the guidance and tracking system 100 may provide trajectories and adjustments to a position (location and orientation) of a biopsy instrument or other medical instrument to facilitate collection of tissue samples in the areas specified in the virtual template 225, including in the anterior zone which is currently not sampled during templated side fire TRUS PBx.

Using one or more user interfaces 200 rendered in a display device 210, an urologist or other medical practitioner may manually segment a prostate or other organ to generate a real, three-dimensional reconstruction by collecting multiple two-dimensional images of the organ, as will be described. A real 3D environment or reconstruction is truly 3D, not a depiction that seems 3D but is actually not, such as stereoscopic views from two slightly offset cameras that give the illusion of 3D but are not really 3D. In some embodiments, the two-dimensional images of the organ may be collected using a transrectal ultrasound probe or other imaging device 120.

In various embodiments, a virtual template 225 can be superimposed on the three-dimensional reconstruction of the organ. For instance, an urologist or other medical practitioner may drag and drop from a template library or a menu a virtual templates having twelve cores (or other suitable amount of cores) on the resulting three-dimensional reconstruction of the organ (FIG. 18A). The template library may be accessed from memory of the computing device 115. Cognitive aids, such as a disk, circle or sphere indicating a template location or encircling a target such as a segmented 3D lesion and a needle stop line, can be precisely overlaid on the TRUS image or a two-dimensional image and/or the real three-dimensional visualization to assist urologists in manually (freehand) steering a transrectal ultrasound probe until a templated location or target is in the needle path (dotted line), shown in FIG. 3A and FIG. 24.

Figure 3B:
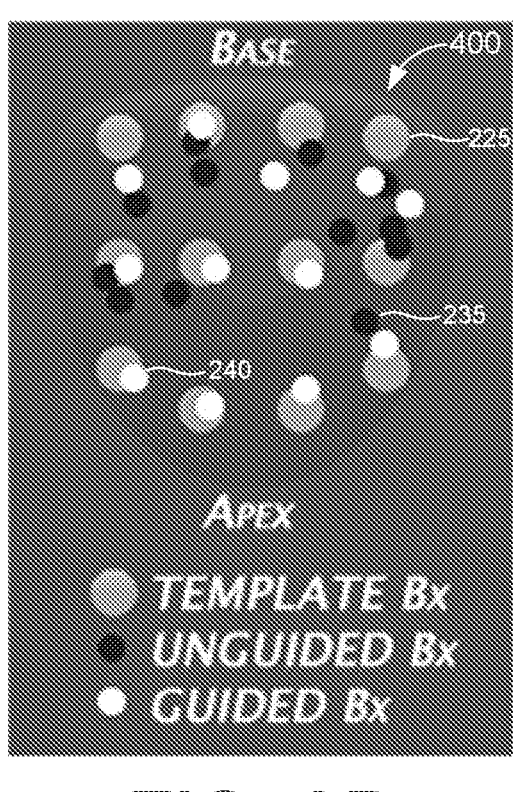
FIG. 3B illustrates the difference between unguided and guided templated biopsy performance in accordance with various embodiments of the present disclosure.

FIG. 3B further illustrates the variations between tissue collection sites performed without the current system (black circles 235) described herein and a twelve-core template (gray circles 225). Notably, the tissue collection sites are not in alignment with the template. However, the tissue collection sites (white circles 240) performed in accordance with the systems and methods described herein show improved alignment with the template, resulting in a more ideal organ biopsy and potentially a significant reduction in false positives.

In FIG. 3B, the gray circles 225 indicate the evenly distributed templated biopsy locations for a 12-core template. The black circles 235 represent biopsy samples using traditional TRUS PBx. The white circles 240 are actual biopsy samples using the tracking and guidance system 100 described herein. Accordingly, a comparison between the white circles 240 and the black circles 235 shows a substantial improvement in collection of tissue samples for the 12-core template.

Template deviation is the average over the n cores in a template of the shortest distance in mm between the center of a sampled core and its intended template location. A simulator was used, as will be described, to assess baseline template deviation and conduct competency-based training. At baseline, prior to simulator-based training, template deviation is above 5 mm in urologists with novices and experienced urologists alike have similar baseline template deviations in the 9-12 mm range. In an evaluation of the new precision PBx tool by a urology resident already trained to competency (template deviation $\leq$5 mm) with the simulator as described herein, deviation (mean$\pm$sd, range) over twelve samples dropped from 5.2$\pm$6.3 (3.1-24.5) to 1.6$\pm$1.8 (1.3-6.6) mm. Also, the actual cores of three urologists using traditional PBx did not sample the apex of the prostate where PCa lesions are commonly located. In addition to collection of a biopsy at an ideal, desired, or templated site, the systems and methods described herein can be employed to aim radiation or delivery of medicines to an organ, lesion, or other portion of a mammalian body, or to place radioactive seeds into a lesion or organ or for other guided interventions.

The embodiments described thus far generally relate to transrectal, side fire, templated, or targeted biopsy. It is fully contemplated and understood that the embodiments described herein and cognitive/aiming aids work equally well for end-fire TRUS biopsy using sagittal and transverse insonation planes (sagittal alone, transverse alone, or both sagittal and transverse together) and also for transperineal prostate biopsy including TRUS-guided transperineal prostate biopsy. It is contemplated that the features and designs described herein are applicable to other guided interventions.

Templated TRUS PBx can be characterized as random biopsy (and is actually also called random biopsy) currently even though it is also called systematic PBx. The embodiments described herein are aimed at making sPBx more systematic and less random. Further, the embodiments described herein provide a way to make templated and targeted PBx truly systematic. The template locations do not represent lesions or regions of interest (ROI) and, in that sense, are not targets even though the user aims at the intended template location to get the cores as close as possible to the template location. The template locations indicate where the biopsies should be sampled so that they are evenly distributed, thus increasing the probability of sampling a lesion if present. As a worst case scenario, imagine a very uneven distribution of cores, where six cores are clustered in the right base and six other cores clustered in the left base. Such patterns have actually been observed. Such a maldistribution of cores indicates that the apex region is not sampled. If a lesion is at the apex region, an undesirable false negative occurs. Thus, the more uniform the distribution of cores, the lower the likelihood of a false negative.

Figure 4:
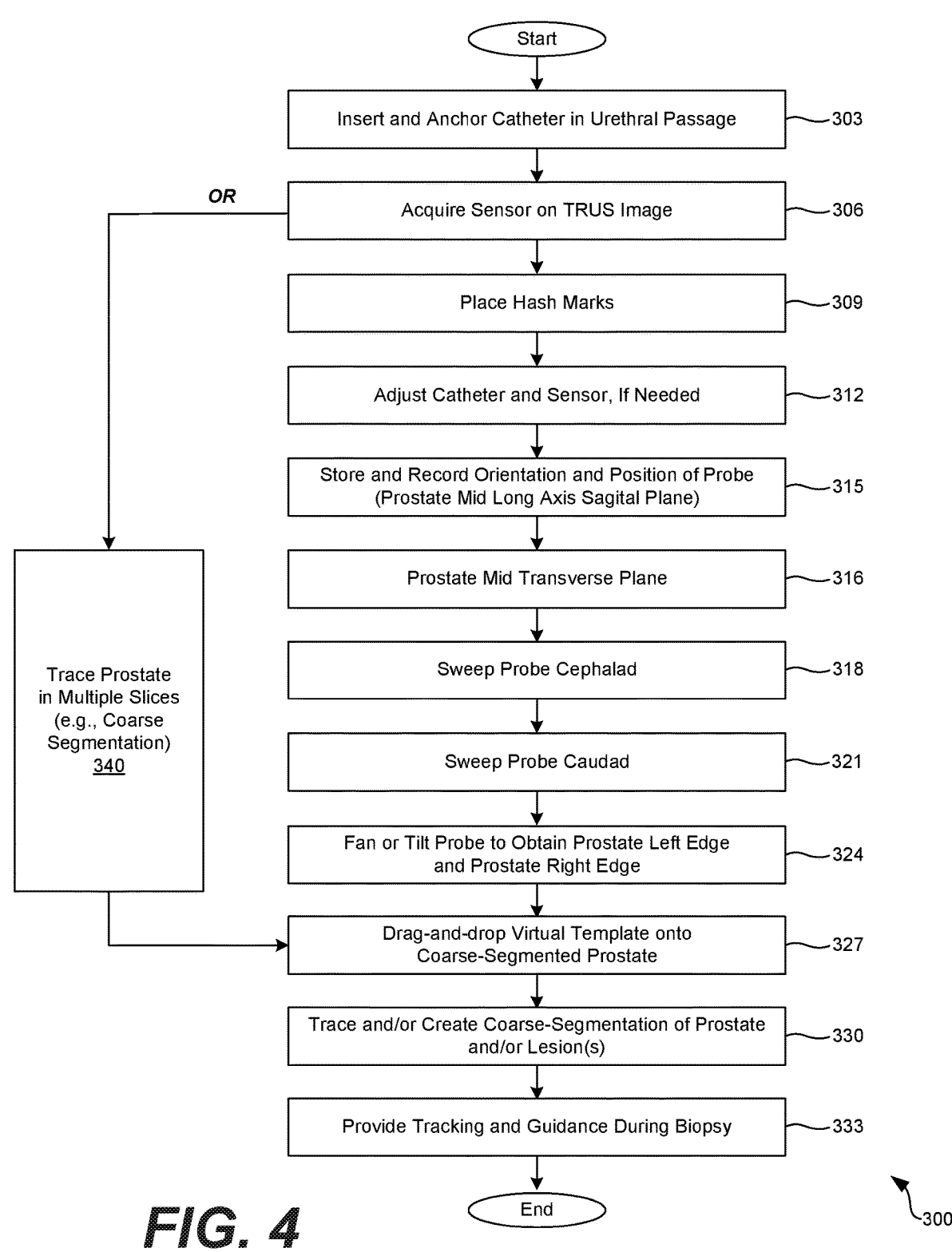
FIG. 4 is a flowchart illustrating an example operation of the guidance and tracking system for templated biopsy or treatment in accordance with various embodiments of the present disclosure.

Referring next to FIG. 4, a flowchart 300 is shown according to various embodiments. Notably, the flowchart 300 of FIG. 4 illustrates an example method of use of the tracking and guidance system 100 described herein. First, at step 303, with a transrectal ultrasound probe or other imaging device insonating sagitally, a catheter may be inserted and anchored into the prostate urethral passage, where the catheter has a six degree-of freedom electromagnetic tracking sensor embedded therein. Other sensors that track less than six degrees of freedom (such as 1-DOF sensors) are contemplated, commensurate with the tracking needs.

Next, in step 306, the sensor or the catheter holding the sensor may be acquired on an image generated by the transrectal ultrasound probe and/or it may be superimposed on the TRUS image as a virtual symbol because the location of the prostate tracking sensor is independently detected by a transmitter such as an SRT (Short Range Transmitter) or MRT (Medium Range Transmitter). In some embodiments, a line that visually goes through the catheter sensor midline is best fit with the catheter long axis, which may be referred to as the prostate long axis.

In step 309, two hash marks may be placed at the long axis on the organ, such as the apex and the base of the prostate. The hash marks may be placed, for instance, by marking on a touch screen type of display device 145 or using a pointing device such as a mouse or trackball. An application on the computing device 115 can then calculate a midpoint between the hashmarks denoting the apex and the base of the prostate or the urethra at the apex edge and base edge of the prostate. A midpoint mark may be added manually or automatically and all three marks (apex, midpoint, base along the prostate midline or long axis) may be shown in the display device 145.

In step 312, the catheter 105 may be adjusted, if needed, so that the sensor midpoint is at the midpoint mark between the apex and the base of the prostate in a given sagittal cross-section. The sensor midpoint is marked manually or automatically for later use. The sensor may be visible in the TRUS or other imaging modality and equi-spaced bands that are also visible in the imaging modality may be used to readily assess distance along the catheter.

In step 315, the application may record and store the location and orientation of the transrectal ultrasound probe relative to the prostate tracking sensor where the sagittal insonation plane contains the prostate long axis, e.g., at mid-sagittal plane where the urethra is visible, and the base and the apex hash marks. The transrectal ultrasound probe can be switched to a transverse insonation plane. The sensor and the sensor midpoint mark previously obtained in the sagittal view is displayed in the transverse plane. The sensor midpoint is differentiated from the sensor body as a different color dot or other shape in the transverse plane. A sweep of the dorsal (rectal) side of the prostate by the TRUS probe may be made horizontally while the transrectal ultrasound probe location and orientation is recorded. The transverse plane is manually adjusted until it passes through the sensor midpoint. The 6-DOF tracking system will know when the transverse plane is at the senor midpoint and the software will inform the user that the desired transverse plane has been obtained. The mid transverse plane going through the sensor midpoint is recorded and displayed, almost orthogonal to the prostate long axis. The mid-transverse plane can be used to detect sensor slip, as described later. The line in the saved transverse plane going through the sensor midpoint in the transverse plane and perpendicular to the long axis is the short axis of the prostate. A multitude of lines can qualify as the short axis based on the above description. The short axis can be denoted and displayed as the line that runs generally parallel to the rectal surface of the prostate, i.e., ideally a "roll" angle of 90° or close to 90°.

In step 318, the transrectal ultrasound probe (transverse insonation plane) may be pushed deeper cephalad and the outermost cephalad edge may be determined. The edge may be marked and displayed as the cephalad plane that is parallel to the short axis plane.

In step 321, the transrectal ultrasound probe (transverse insonation plane) may be pulled shallower and the outermost caudad edge may be determined. Again, the edge may be marked and displayed as the caudad plane that is parallel to the short axis plane and the cephalad plane.

In step 324, the TRUS probe may be repositioned and switched to the sagittal insonation plane, for instance, with the patient in the usual left lateral decubitus (i.e., the patient lying on their left side). An operator may fan or roll the transrectal ultrasound probe down (clockwise) to acquire the leftmost edge of the prostate, which may be stored and displayed as the prostate left edge. With the transrectal ultrasound probe still in sagittal insonation mode (i.e., with the patient in the usual left lateral decubitus or, in other words, the patient lying on their left side), the transrectal ultrasound probe may be fanned or rolled up (counter-clockwise) to acquire the rightmost edge of the prostate, which may be stored and displayed as the prostate right edge.

As may be appreciated, five planes have been generated (caudad, cephalad, short axis, left edge, right edge) and two lines (prostate long axis and prostate short axis) may be stored and displayed. Further, two TRUS locations and orientations relative to the sensor may be shown that align with the long axis (sagittal insonation mode) and the short axis (transverse insonation mode). The four planes (caudad, cephalad, right, left) create a prostate "box" or organ box. With the transrectal ultrasound probe in the transverse insonation mode, the transverse planes may be shown parallel to the short axis plane. In some embodiments, they may be shown spaced 5 mm (or other suitable dimension) apart on each side of the short axis plane. The user may be instructed to sequentially move (push or pull) the transrectal ultrasound probe so the transverse insonation plane matches each of the spaced planes. After matching each plane, the user may be instructed to identify the outermost right and left edge of the prostate on the TRUS image for that transverse plane, which are marked and stored.

In various embodiments, after marking and identifying the right and left edges of the prostate, the application may display a plan view of the prostate, i.e., a posterior-anterior (PA) view (user looks at the prostate from the back of the patient), having dots denoting the right and left edge of the prostate previously marked on the uniformly spaced transverse planes. The dots may be automatically or manually connected to create an outline of the prostate in the PA view. The PA coronal outline of the prostate may be stored and shown in the display device 145.

In another embodiment, instead of steps 306 to 324, the process can proceed to step 340 where the user can trace the outline of the prostate on the ultrasound screen using a touch screen or pointing device at multiple planes from a multitude of ultrasound probe locations and orientations, ideally using both sagittal and transverse planes. Referring back to FIG. 4, the traced outlines can be saved as 3D objects and registered to the prostate sensor space; in other words, the traced outlines are attached to prostate sensor space and, as a consequence, move when the prostate sensor moves in response to pressures and forces applied by the TRUS probe.

As the user traces the prostate at multiple planes, a wire mesh-like shape of the prostate can be constructed in the computing device 115. In one embodiment, the points used to create the traced outlines are converted into 3D objects using a point cloud to mesh algorithm that creates a 3D object as an output given a set of 3D points as input. In a reduction to practice of one embodiment, we performed the point cloud to mesh conversion in real-time using Unity3D software.

Figure 6:
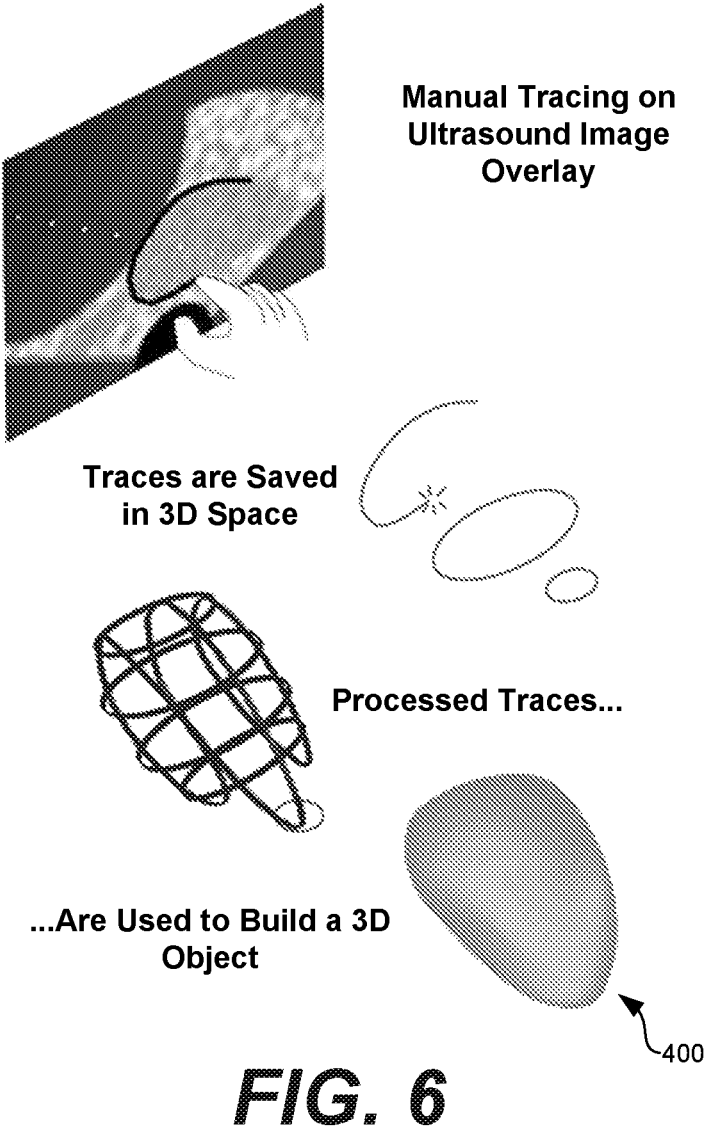
FIG. 6 is a schematic diagram illustrating a manual tracing of an organ and/or three-dimensional object, such as a prostate or lesion, to create a three-dimensional reconstruction of the organ or object in accordance with various embodiments of the present disclosure.

A "freeze" function can be activated that freezes the ultrasound image before each trace so the user need not struggle to trace a moving target (if the TRUS probe moves during tracing) and frees both hands for solo use (without an assistant), if necessary. That is, the TRUS probe does not need to be held in place in the rectum while the manual tracing occurs. The computing device 115 can display an approximated 3D volume that fits all the manual traces producing a 3D shape that is a coarse segmentation of the prostate that occurs in clinic during the biopsy procedure and precedes the actual sampling of cores. The 3D shape becomes more accurate as new traces are added, as shown in FIG. 6. An "undo" function can allow the user to reject incorrect traces without having to start over.

In one embodiment the computing device can detect sparsely-traced areas of the three-dimensional model and request that the user fill in the gap by adding traces from specific ultrasound probe locations and/or orientations. In another embodiment, the 3D model can be constructed automatically by a software algorithm that uses a neural network or other software such as edge detection algorithms to recognize the boundary of the prostate or other landmark or organ in the ultrasound image, replacing the need and the time for a human user to manually trace the outlines on TRUS images. The 3D model can also be saved to a library for later use. Once the 3D volume is sufficiently constructed, it is used for fitting and adjustment of a virtual 3D template to the newly coarse segmented prostate for placement, sequencing and, if needed, addition of template locations for sampling additional cores.

In step 327, while in the PA view, for instance, the user can be instructed to drag-and-drop a pre-arranged virtual template 225 onto the prostate. As noted above, in some embodiments, the virtual template 225 may include a twelve-core template. In some embodiments, the operator may manually slide each of the template locations (e.g., 12 in the commonly-used double sextant schema), referred to as cores, that may fall outside the prostate onto the prostate or other organ. The task of determining if a core will sample non-prostatic tissue (i.e., some or hopefully not, all of the core is outside the prostate) is facilitated if the option of displaying 3D cores is selected instead of using circles to represent template locations. In various embodiments, the template locations (e.g., twelve) may be displayed as cylinders, spheres, icons, or other suitable visual indicators and can be manually placed in the anterior region of the prostate. Users can also select as many template locations as needed and are not limited to the number of template locations specified in commonly used template schema. Users may change the order of the template locations or accept the default template location sequence.

Figure 18:
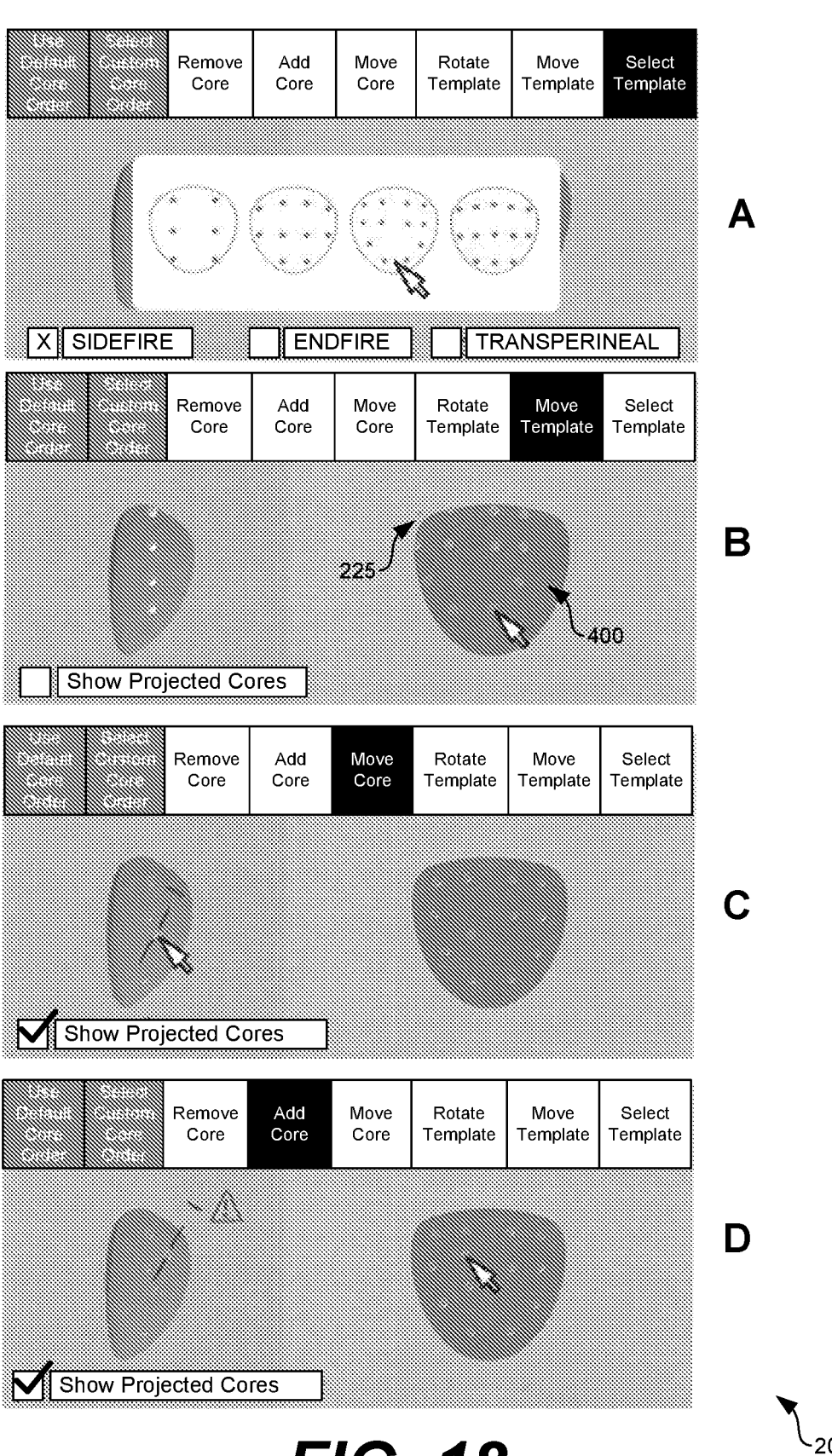
FIG. 18 is a user interface for pre-planning and adjustment by the user of template locations and cores in accordance with various embodiments of the present disclosure.
Figure 19:
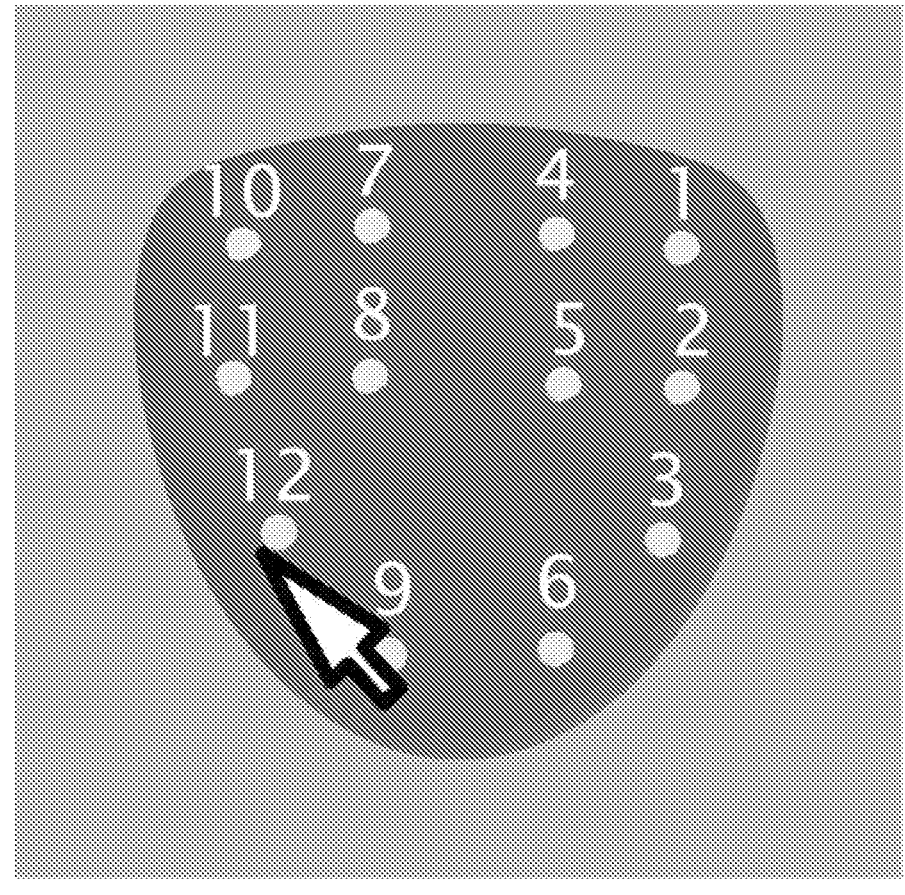
FIG. 19 is a detail of a user interface for pre-planning template locations that shows a user selecting a desired order or sequence of cores on the template in accordance with various embodiments of the present disclosure.

One example of the template editing process is shown in FIG. 18. Referring to Row A, of FIG. 18 an example user interface 200 is shown for selecting a given template schema from a menu of templates. FIG. 18 shows the coronal (PA; posterior-anterior) and sagittal views but embodiments described herein also contemplate using a transverse view that can be helpful in avoiding the urethra and bladder when aiming for anterior zone template locations. Row B of FIG. 18 shows the user moving the template into position by dragging it onto the real 3D reconstructed prostate. There is an option to rotate the entire template set about different planes such as the coronal and sagittal planes.

Row C of FIG. 18 shows the user moving an individual core or template location. The user first clicked the 'Move Core' button, then selected a core in the coronal view (on the right of the diagram). The user then dragged the core slightly anterior and caudad (shown). The projected core and maximum needle tip penetration distance for a side fire needle guide is superimposed on the sagittal view. The sagittal view used for template modification takes into account the pose of the prostate relative to the TRUS probe longitudinal axis and the angle of the side-fire needle guide to the TRUS probe longitudinal axis (e.g., ~19°). The TRUS probe longitudinal axis is depicted as vertical in the user interface shown in FIG. 40. The pose of the coarse-segmented prostate relative to the TRUS probe axis (vertical line) is replicated based on the previously acquired and saved spatial relationship between the TRUS probe and the prostate during coarse segmentation. Row D of FIG. 18 shows the process of adding a new template location. The user clicked 'Add Core' and clicked in the coronal view to add a new core at the cursor position (shown). The projected core and maximum needle penetration distance for a side fire needle guide is superimposed on the sagittal (or transverse) views for the new core or template location. Note that a perfectly aligned biopsy needle for that newly-added template location will place the needle tip far outside the prostate, triggering a graphical and audible alert to the user. The user's next action should be to move the new template location towards the apex to prevent injury on the other side of the prostate and sampling of non-prostatic tissue. In some embodiments, a segmented 3D bladder or 3D urethra or 3D seminal vesicles can be used, segmented, and displayed as "no-go" 3D regions for the planned needle path or core.

In step 330, the operator may manually trace the outline of any lesion or suspicious shadow or region of interest (ROI). Additionally, the operator may create coarse 3D segmentation of lesion(s) to produce 3D lesions or ROIs that are used for guidance, in the 3D visualization and as overlay in the TRUS image (display as an overlay the intersection of the TRUS insonation plane with the 3D lesion or ROI). The operator may also create coarse 3D segmentation of any no-go areas to be avoided, such as the bladder, urethra, seminal vesicles, or tracked urethral catheter or urethral catheter cuff. Alternatively, the template fitting and adjustment could be pre-existing imaging data for an object obtained from a third party or another source such as a segmented 3D prostate from an MM scan after the pre-existing object has been imported and registered to the prostate sensor space.

Finally, in step 333, guidance and tracking may be provided during a biopsy or other medical procedure or guided intervention described herein. More specifically, the medical instrument and the prostate (or other organ) may be shown in real-time, for instance, as the transrectal ultrasound probe is manually moved, cognitive aids will display where a biopsy core (i.e., a tissue sample) will be taken and how it compares to where the template location is and provide guidance to steer the predicted core to the desired template location or to a targeted lesion or ROI. The overlay of cognitive aids occurs both in the TRUS images and in the 3D visualizations. In various embodiments, three orthogonal preset camera views may be shown in the display device 145 to avoid "parallax" error that may occur when aligning objects from one 3D perspective, such as a grey core with a green core. The TRUS probe may be repositioned by the operator until a yellow cylinder matches a template or core location (i.e., a green dot for a core center or a green cylinder for a core in some embodiments). When aligned, the operator may trigger a biopsy instrument to collect a tissue sample at an ideal or desired location and orientation. The procedure may be repeated for the other eleven (or other amount) of templated locations in the given or user-modified template schema. In various embodiments, a check mark or other visual indicator appears on the already sampled template location or the location is no longer displayed so that only the locations still to be sampled are displayed creating a minimalistic interface and display. Alternatively, the already sampled cores may still be displayed in the template, TRUS and 3D visualization but in a different color from those cores still to be sampled. Displaying already sampled cores helps prevent sampling the same template location more than once. The systems and method described herein may be used on a patient during a medical procedure, as well as on a cadaver or in a simulation that utilizes a TRUS PBx simulator.

During guidance, the orientation of the default ultrasound image on the screen does not mimic the real world position of the insonating plane (see FIG. 9A, showing a sagittal plane). An option can be made available that rotates the ultrasound image to mimic the position of the real insonating plane from the user's perspective when holding the TRUS probe inside the patient's rectum (see FIG. 9B).

According to various embodiments described herein, a virtual, real-time, real three-dimensional (real 3D) visualization system for mapping and guiding an instrument to a desired location and orientation or target is provided. As such, any feedback or guidance provided to an operator (e.g., an urologist or other medical practitioner), may be visual, audio, tactile and in three-dimensions.

In various embodiments, multiple views of an organ may be provided. The multiple views may include two-dimensional and/or three-dimensional views. As such, parallax error may be addressed using the multiple views. In some embodiments, the multiple views may be orthogonal views. The prostate or other organ may be tracked by a sensor which, in some embodiments, may be positioned in the urethra of a patient using a catheter.

In some embodiments, the tracking sensor may be electromagnetic and may be tracked by a transmitter. While several of the embodiments described herein relate to prostate biopsies, the systems and methods described herein may also be performed during radiotherapy, radiosurgery, ablation, HIFU, administration of a drug, access into spaces (such as thoracic paravertebral or epidural space) and vessels (such as the internal jugular for central venous access), and other guided interventions and therapeutic procedures where the treatment must be precisely aimed to prevent collateral damage and properly aimed such that surrounding healthy tissue is not irradiated or otherwise harmed.

In various embodiments, a virtual, three-dimensional, real-time visualization system for mapping and guiding a needle, tool or an imaging probe to a desired location and orientation or target are described. As noted above, in some embodiments, the needle or probe may include a sensor that is tracked by a transmitter. Further, a tracked needle may be used for regional anesthesia or central venous access, as well as injection, biopsy, monitoring, ablation, abscess drainage, fine needle aspiration or other medical procedure and guided intervention.

In some embodiments, the tracked needle is a biopsy needle that may be part of a biopsy instrument. The tracking of the needle may provide precise calculations and predictions in real time of where a biopsy core will be sampled, for instance, if the biopsy instrument is triggered. The predicted core may be displayed as a graphical icon and updated in a real-time, real three-dimensional, virtual visualization as the needle gun is adjusted in space and time. In some embodiments, the target or template location and orientation may be depicted as an icon or other visual indicator.

As may be appreciated, an operator may use the three-dimensional visualization to move a tracked needle to match the predicted core to the desired core location (templated or targeted) and fire the needle gun when the two overlap or are in close proximity. In some embodiments, the triggering of the biopsy instrument may be performed automatically, for instance, when the predicted core is aligned with the desired core.

Figure 23:
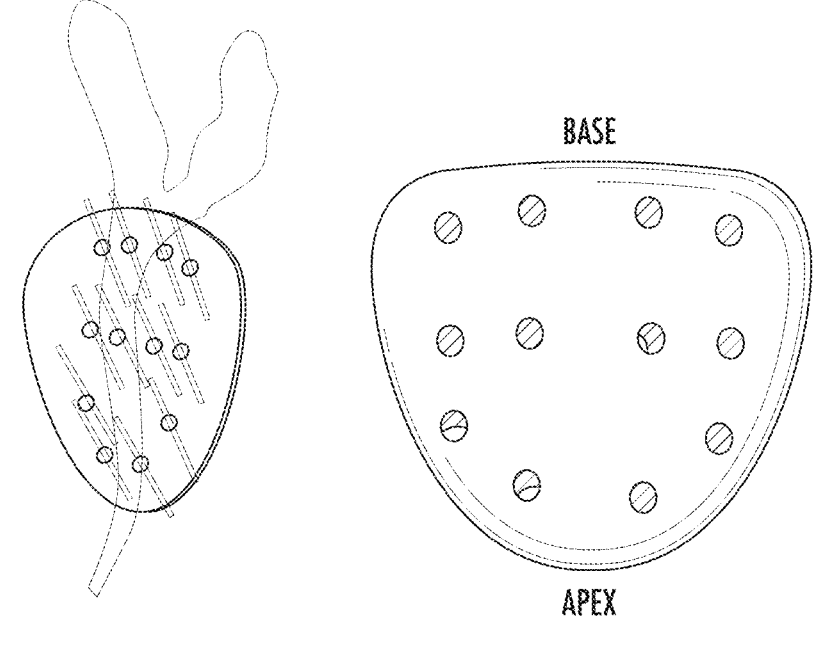
FIG. 23 shows performance of a user using the proposed system in a simulator mode in accordance with various embodiments of the present disclosure.

Preliminary Data: A transrectal ultrasound PBx simulator was created and a precision PBx tool was designed that does not require an MRI or a radiologist. The deviation over 12 samples dropped from 5.2±6.3 to 1.6±1.8 mm. FIG. 23 shows a good example; the template deviation of this attempt is 0.7 mm. The actual cores of three different urologists using traditional PBx did not sample the apex of the prostate where PCa lesions are commonly located. Other preliminary data include (1) Prostate biopsy false negatives are related to template deviation (p=0.0015) abstract submitted to AUA 2020 meeting on Nov. 1, 2019; (2) template deviation is related to TRUS probe pitch (p=0.000167)— abstract submitted to AUA 2020 meeting on Nov. 1, 2019; (3) paper describing a pitch-neutral technique submitted to Journal of Urology; (4) Cadaver experimentation around July 2019 or later: A Model 90 6-DOF electromagnetic sensor from NDI was fitted into the bore of a 14 Fr Bard Foley catheter through 2.0 mm PTFE tubing. The cadaver test protocol included pushing and pulling on the urinary catheter with the imbedded Model 90 electromagnetic sensor inside the urinary catheter while the urinary catheter cuff was inflated inside the prostatic urethra to determine visually (via ultrasound image) if the catheter (and therefore the imbedded sensor too) slipped relative to the prostate. The sensor did NOT slip relative to the prostate which was the desired result. The ultrasound machine model can include SonoSite M-Turbo TRUS Probe or the SonoSite ICTx/8-5 MHz The inflation of the Foley urinary catheter cuff with about 1.5-2 ml saline could be observed in the TRUS image. The inflated cuff could also be observed in the TRUS image. The bubbles in the saline in the cuff cast faint shadows.

The Foley urinary catheter remained anchored in the prostate when the cuff was inflated inside the prostatic urethra. Only 1.5-2 cc of saline solution causes the surrounding tissue to move with, i.e., follow the Foley urinary catheter, indicating secure anchoring. The small volume of saline will be enough to anchor the urinary or urethral catheter without causing undue discomfort in the patient.

The urinary catheter was easy to see in the TRUS image during the cadaver experimentation. Live real time feed of a TRUS machine video output (GE LOGIQ S7, BK Medical FlexFocus 400) to a laptop (Microsoft Surface Pro) occurred with no noticeable latency and without aspect ratio warping. This indicates that relying on real-time, distortion-free video transfer of the TRUS image is feasible for a retrofit kit embodiment.

Detection of Tracking Sensor Slip Relative to Prostate. A coarse segmentation process described herein can be dependent on a prostate tracking sensor in the catheter 105 inserted in the urethra not moving with respect to the prostate or the catheter 105. If the prostate tracking sensor slips (e.g., if the tracked urethral cuff slips relative to the prostatic urethra), then an operator must be alerted to compensate for the slip by either moving the three-dimensional virtual prostate back into alignment with the physical prostate displayed in the TRUS image, or again reconstructing the three-dimensional virtual prostate. The urethral catheter 105 can slip relative to the prostate in two primary ways: axially along the longitudinal axis of the urethra or rotationally where it spins inside the urethra. The sensor can also slip relative to the catheter 105 which would also throw off the prostate tracking. The slip detection feature will detect all the above types of slip.

Figure 20:
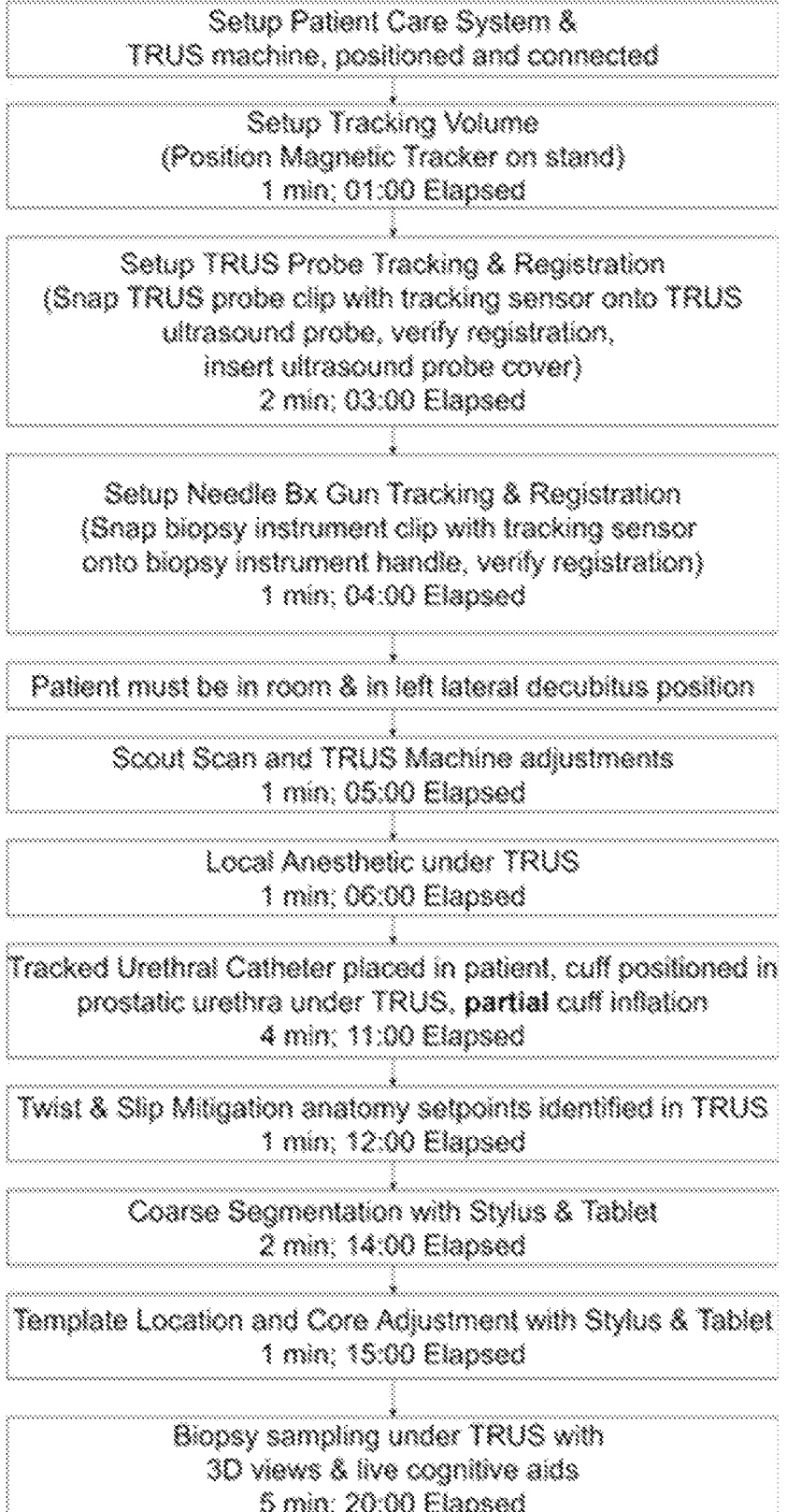
FIG. 20 is a process of an embodiment of the system applied to systematic prostate biopsy using a retrofit implementation in accordance with various embodiments of the present disclosure.

FIG. 20 shows a flowchart of the necessary steps for preparing and using the system are shown with expected times that an experienced user(s) may take for each step (~20 minutes or less for an entire procedure). A quality control process is also described that determines in real time if the prostate tracking sensor has moved relative to the prostate using external-to-prostate landmarks, such as seminal vesicles or the bladder, and internal-to-prostate landmarks, such as the junction of ejaculatory ducts and urethra or the entry and exit ports of the urethra in the prostate. The process requires a user to identify and mark reference landmarks in the TRUS image similar to manual segmentation after the tracked urethral catheter is placed and anchored. In one embodiment, the user visually places anchors (by inflating the cuff) and the prostate sensor in the TRUS image at a midpoint between the urethra entrance at the base of the prostate and the urethra exit at the apex of the prostate. In another embodiment, a midpoint can be generated automatically, instead of manually and visually, by the user. In a mid-sagittal TRUS image that usually includes the entire prostatic urethra, the user identifies and marks the urethra entrance at the base of the prostate and the urethra exit at the apex of the prostate using a touchscreen and the TRUS image. The midpoint between these two points is calculated by the tracking application 215 or the guidance application 220, and displayed on the TRUS image.

The urethral catheter 105 is advanced until the midpoint of the prostate sensor is aligned to the midpoint in the TRUS image. The reference landmarks are virtual three-dimensional objects that can be visible as overlays in the live TRUS images. To set up the slip detection feature, after the urethral catheter 105 has been placed, the user will first acquire a mid-sagittal view that includes the entry and exit of the prostatic urethra with the prostate sensor and urethral catheter. In general, but not always, at the mid-sagittal plane, the urethra will be visible in the TRUS image in its entire length and therefore the urethral catheter will also be visible too along its entire length. In addition, the prostate tracking sensor is visible in the TRUS image and can also help the user visually detect if the sensor has slipped relative to the prostate. After acquiring the mid-sagittal plane, the user will mark the entry into and exit from the prostate of the prostatic urethra on the TRUS image via a touchscreen and use them as reference landmarks that we call virtual landmarks. The entry and exit reference virtual landmarks are saved to prostate sensor space as well as the TRUS probe position. Axial slip (unwanted movement of the sensor up or down the urethra passing through the prostate) is monitored and detected by verifying that the sensor remains at the midpoint between the apex and the base at the prostate sagittal midline. All TRUS probe positions used for obtaining landmarks and coarse segmentation are automatically saved to prostate sensor space.

The user will then adjust the position of the TRUS probe and use the transverse TRUS image (in a TRUS probe with dual insonation planes) and mark edges of external landmarks like seminal vesicles and bladder, internal to prostate landmarks like ejaculatory ducts or the junction of the ejaculatory ducts with the urethra, or by tracing an outline of a transverse plane of the prostate. These transverse virtual landmarks are also saved to the prostate sensor space as well as the new position of the TRUS probe when this new set of landmarks was acquired. Rotational slip between the tracking sensor and the prostate is monitored and detected by verifying that the transverse landmarks described above overlay their real counterparts in the TRUS image. The sagittal and transverse profiles (prostate edges) traced during coarse segmentation are saved and used as landmarks for detecting slip of the tracking sensor relative to the prostate. The saved outline is displayed on the TRUS image and compared to the actual outline of the prostate in the TRUS image when the TRUS probe is at the previously saved position for that prostate profile.

If the saved profile and the actual profile match, there is no slip. If there is a mismatch, then slip occurred. These comparisons can be done both visually or automatically using edge detection software or neural networks. In one embodiment, a timer can remind a user to check prostate alignment at set time intervals and, if necessary, guide the user to the exact TRUS probe position that was used to save the landmarks. If the TRUS probe position cannot be physically recreated, it would indicate that significant slip of the sensor has occurred relative to the prostate. In another embodiment, the verification for axial and rotational slip can be done automatically via feature recognition software of the landmarks in the TRUS image using a neural network that has been trained to recognize landmarks in ultrasound images such as prostate boundaries, ejaculatory ducts, seminal vesicles, and bladder. An automatic slip detection routine can replicate the manual tasks previously described above. In one embodiment, if a software routine detects possible prostate sensor slip, a user can be alerted to visually verify that the prostate sensor has not slipped by guiding the user to a saved probe position associated with a virtual landmark and displaying the virtual landmark(s) in the TRUS image. The virtual landmark can overlay its corresponding landmark in the TRUS image. The user can then visually verify that the virtual landmarks and the corresponding landmarks in the TRUS image still match. If they do not match, the prostate sensor has slipped and the user can compensate for the slip as described above. Slip is unlikely based on preliminary experiments performed with cadavers using a 14 Fr Bard urinary catheter and a SonoSite M-Turbo TRUS machine with an ICTx/8-5 MHz TRUS probe.

Automatic, Patient-Specific Templates. Manual adjustment by the user of the template was described during a pre-biopsy planning stage. In a different embodiment, a virtual three-dimensional template is automatically created specific to each individual prostate. A software routine can take a three-dimensional reconstruction of the prostate as an input and outputs a three-dimensional template optimized to the specific prostate that minimizes the probability of a hypothetical lesion of a given shape (e.g., spherical) and size (e.g., 1 cm dimeter sphere) not being sampled. In the case that assumes a spherical lesion 1 cm in diameter, a capsule (1 cm diameter cylinder with hemispherical ends) is concentric to the core. The user can change the capsule diameter to other values, including for different parts or regions of the prostate. The software routine can determine the prostate volume outside the capsules and automatically move the core positions to minimize the prostate volume outside the capsules.

Users can select a threshold for the maximum prostate volume outside the capsules that they will allow and add more cores to get the volume below the threshold, if the threshold is exceeded. Users can also select the size of the hypothetical lesion such as the lesion diameter. In another embodiment, the software routine monitors biopsy core placements and accounts for user error in placing the core at the template location. That is, during the PBx procedure, the software routine accounts for the template deviation in the cores that have already been collected. For each template location already sampled, the software routine automatically adjusts the template locations still to be sampled based on the deviation of already sampled biopsy cores. The adjustment is done by minimizing the prostate volume outside the capsules by adjusting the position of the template locations that still need to be sampled.

Tracking Freehand Needle via Tracked Needle Guide. In an embodiment for a retrofit kit, a tracking sensor is in a removable clip that snaps onto the handle of the needle biopsy instrument, such as the biopsy gun 125. In a non-retrofit embodiment, the tracking sensor is placed near the core chamber (e.g., the section of the needle that grabs the sample). In a retrofit embodiment, tracking the needle during freehand transperineal biopsy is challenging because the biopsy needle is tracked from the biopsy instrument handle, not near the core section. The biopsy needle is long and flexible (bends) so that the sensor in the handle cannot reliably track the core cutting section when bending occurs. "Freehand" transperineal PBx does not use a TRUS probe needle guide that provides intrinsic mechanical alignment of the needle with the TRUS sagittal insonation plane. Therefore, the needle is unconstrained and it is hard to get the needle aligned with the TRUS insonation plane so that it becomes visible in the TRUS image.

To overcome these issues, rigid needle sheath(s) that look like needles or catheters made of a material that does not interfere with tracking (such as cobalt-chromium or titanium for electromagnetic tracking) can be placed in the transperineal region but not deep enough to penetrate the prostate. The rigid needle sheath is tracked via a 6-DOF sensor in the needle hub. The biopsy needle is inserted into the sheath and the needle path and position is inferred from the sensor at the hub of the rigid sheath. In another embodiment, the needle sheath made of a material that does not interfere with tracking such as non-ferromagnetic metals for electromagnetic tracking is mechanically and rigidly coupled to the TRUS probe so that as the TRUS probe moves, the needle sheath remains aligned with the sagittal insonation plane of the TRUS probe. This mechanical coupling makes it easier to view the needle in the TRUS image during transperineal biopsy. The needle sheath then acts as a needle guide for transrectal needling but for transperineal biopsy. Like previously described, the needle sheath is mechanically affixed to the TRUS probe no longer needs to be tracked by a 6-DOF sensor. A 1-DOF sensor to determine needle insertion depth may suffice and can be mounted on the clip that fixes the needle sheath to the TRUS probe and maintains the needle in the TRUS probe insonation plane.

Automatic Virtual Marking of Sampled Biopsy Core Immediately Upon Triggering the Biopsy Instrument. Existing fused biopsy systems mark biopsy cores by requiring an assistant to click a button on a user interface after the core is sampled. In other words, after the biopsy instrument is fired and the biopsy needle springs forward to capture a sample, a user interface button must be clicked to tell the software that a biopsy was just taken in current systems. If the user interface button is not clicked, the core is not marked. If there is a delay in pressing the user interface button to mark the core, the biopsy needle may have drifted or the patient may move in response to biopsy needle movement and the position of the already sampled core will be marked incorrectly.

Figure 21:
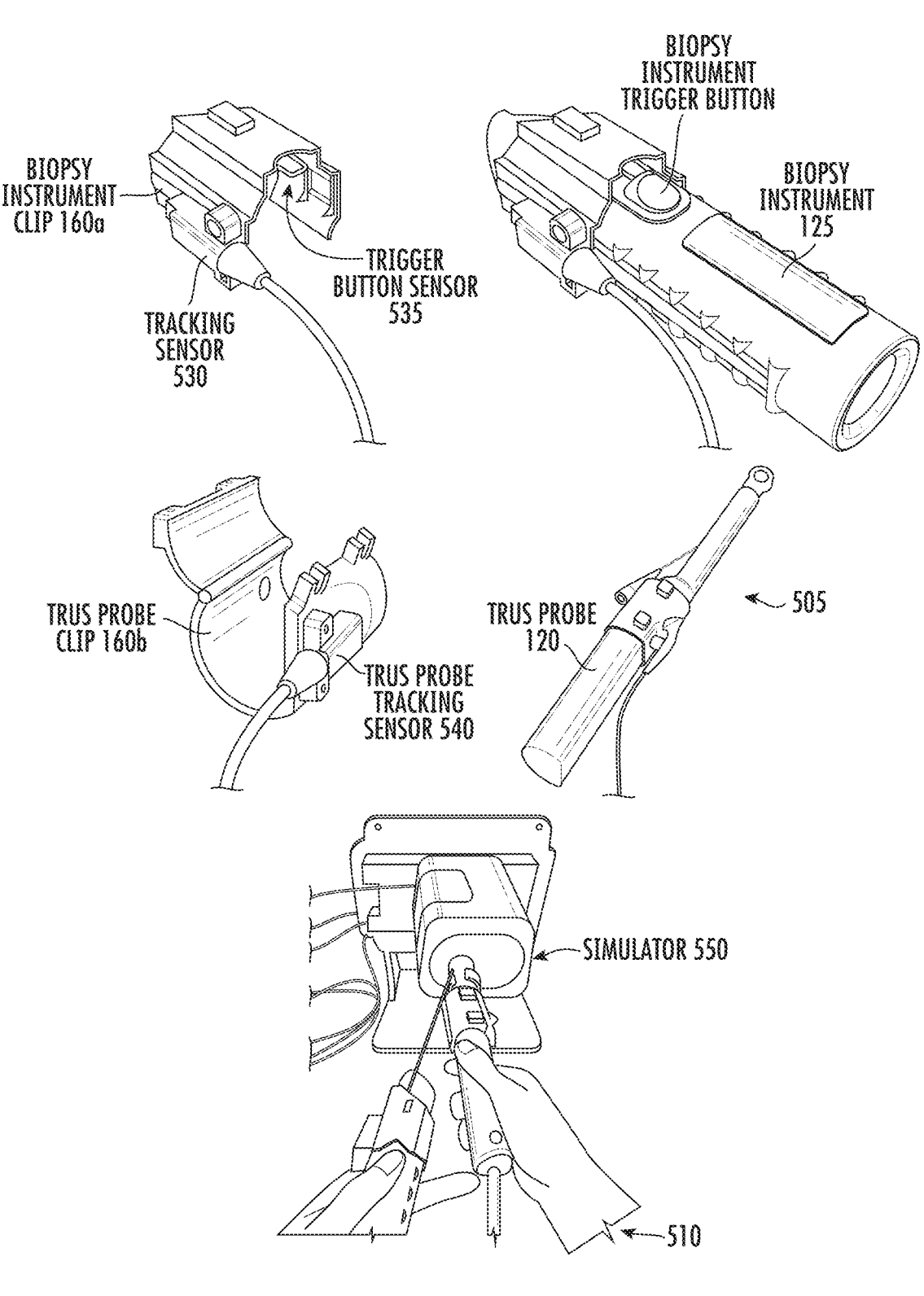
FIG. 21 provides detailed illustrations and a photograph of a retrofit implementation of a cleanable tracked biopsy needle clip and a cleanable tracked TRUS probe clip in accordance with various embodiments of the present disclosure.

The top left portion of FIG. 21 shows a biopsy instrument clip with a 6-DOF tracking sensor and trigger activation sensor (switch) designed to fit a Bard Max-Core Disposable Core Biopsy Instrument. The top right portion of FIG. 21 shows the biopsy instrument clip in place on a Bard Max-Core Disposable Core Biopsy Instrument. The middle left portion of FIG. 21 shows a TRUS probe clip with a 6-DOF tracking sensor designed to fit a BK Medical Prostate Triplane 8818 ultrasound probe. The middle right portion of FIG. 21 shows the TRUS probe clip with tracking sensor in place on a BK Medical Prostate Triplane 8818 ultrasound probe. The bottom portion of FIG. 21 is a photograph of the biopsy instrument and the TRUS probe shown above (both with three-dimensionally printed tracked clips) being used on a simulator used to conduct sPBx training. In various embodiments, the clips can be disposable or single use after removing the tracking sensors from the clips before discarding the clips. The expensive sensors are then inserted into new clean clips for re-use of the sensors. In yet another embodiment, the sensor is disposable.

In one embodiment of the retrofit kit, the biopsy instrument clip 515 (see FIG. 21) contains a sensor 530 or switch that automatically and instantly sends a signal to the computing device 115 running the guidance application 220 at the instant that the biopsy instrument trigger slide is pushed or activated indicating that a biopsy core has just been sampled. The trigger activation sensor can include a physical switch in the biopsy instrument clip 515 that is activated when the biopsy instrument trigger slide is pushed forward to fire the instrument. The trigger switch can be placed in a housing that is shaped so that the switch is out of the way of the user's finger. In other words, the housing shape prevents the user from accidentally activating the trigger switch without actually pressing the biopsy instrument trigger. The switch housing prevents incorrectly marking a core as sampled when it actually has not been sampled. In another embodiment, the biopsy instrument trigger slide does not physically activate a trigger switch; instead, a trigger button sensor detects the unique sound or vibration of the biopsy instrument firing. In yet another embodiment that is not a retrofit kit, the trigger switch is built into the biopsy instrument.

Figure 22:
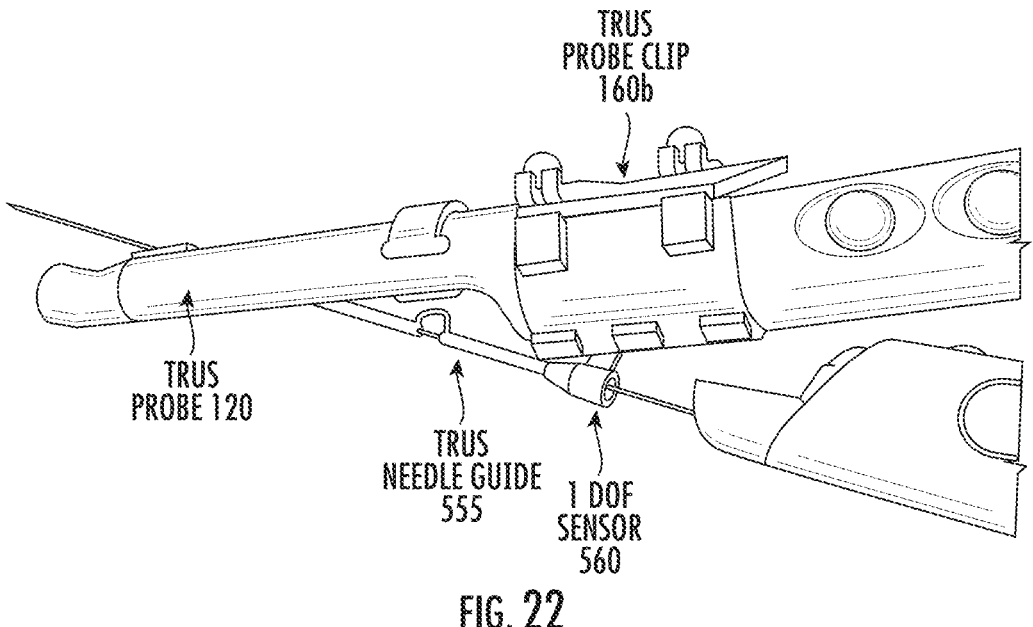
FIG. 22 is an embodiment of a tracked TRUS probe with rigidly attached needle guide with a 1-DOF sensor at the needle guide entry hole in accordance with various embodiments of the present disclosure.

1-DOF Needle Excursion Sensor. 6-DOF sensors are currently more expensive than 1-DOF sensors 560. An embodiment of a tracked TRUS probe with rigidly attached needle guide with a 1-DOF sensor 560 at the needle guide entry hole is shown in FIG. 22. In this embodiment, the biopsy needle does not have a tracking sensor and any commercial needle biopsy instrument can be used. The needle position is inferred using the needle guide rigidly attached to the tracked TRUS probe 120 and a 1-DOF sensor 560 on the tracked TRUS probe 120 that measures how much of the needle has passed through the 1-DOF sensor 560, that is, the depth of insertion of the needle is measured allowing the real-time overlay of the needle and needle tip over the TRUS image. The 1-DOF sensor 560 (e.g., a rotary position sensor, rotary potentiometer, or optical sensor such as those used in optical mice) is attached to the TRUS probe clip 525 in one embodiment (FIG. 21) and in other embodiments could be built into the TRUS probe 120 itself. It is to be understood that features of a retrofit kit are described in detail, those features are generally contemplated to be also built into new systems and devices.

Needle In Needle Guide Detection. Cognitive aid overlays on the TRUS image related to biopsy needle location (e.g., stop line, predicted core, etc.) should not be enabled unless it is known that the needle is in the needle guide. Similarly, the guidance application 220 should ignore a signal that the biopsy instrument trigger was pressed if the biopsy needle was outside the patient, for example, during handling between biopsies. Therefore the tracking application 215 and/or guidance application 220 must know when the needle is placed in the TRUS probe needle guide, instead of being held next to the TRUS probe 120 or close to the needle guide, as occasionally occurs during normal handling. When the biopsy needle is flexible and long and the tracking sensor is on the biopsy instrument handle or clip instead of the needle tip, determining when the biopsy needle is truly inside the TRUS probe needle guide can be complicated. The guidance application 220 can verify that the biopsy needle has been inserted in the needle guide using feature analysis of the sagittal or transverse TRUS image. In one embodiment, a neural network trained to recognize needles in an ultrasound image is used to automatically detect if the needle has been inserted into the needle guide. In another embodiment, a software routine can look for the needle in the ultrasound imaging in the sagittal or transverse plane by inspecting the pixels in the region in the TRUS image where the needle will first appear (i.e., the part of the TRUS image next to the needle guide exit).

Importing and Registering Externally Acquired Targets into Sensor Space. Prostate biopsy is used as an example of importing and registering externally acquired targets into a sensor space. In one embodiment, the system 100 can perform targeted biopsy in addition to systematic template biopsy. In a Mass General study, 16% more cancer was detected when a systematic (templated) biopsy was done following an MRI/US guided fusion prostate biopsy, illustrating the benefits of being able to perform both targeted and systematic biopsy with one biopsy system. An approach is described to make the system 100 able to perform targeted PBx in addition to sPBx. The system 100 can import data from other imaging scans, such as MRI or CT, for those patients who have pre-existing imaging data and register the data such as target (lesion and ROI) shape, size, location, and orientation into the coordinate system of the prostate sensor space, the three-dimensional reconstruction (e.g., the three-dimensional lesion or ROI is visualized in 3D in the 3D visualization), and cognitive aids (e.g., the 3D lesion or ROI is shown in 2D cross-section as a cognitive aid within the TRUS image). Importation and registration are accomplished in three steps. Step 1 can include accessing the MM scan and, if needed, segmenting (including the coarse segmentation previously described) the prostate and/or targets into 3D objects, if segmentation has not already been performed. Segmenting can be performed ahead of the PBx procedure, but is not mandatory. Software packages are also available to create three-dimensional objects from MM scans (InVesalius, ITK-SNAP). Ideally, the entire prostate can be segmented into a three-dimensional object, not just the targets or ROIs.

Step 2 can include importing the segmented or non-segmented data into the software three-dimensional environment, i.e., the coordinate system of the prostate sensor space. Step 2 can also be performed ahead of the PBx procedure. A rough registration into the tracked volume covered by the tracking transmitter is done that anticipates the patient position (e.g., left lateral decubitus, lithotomy, etc. position). This is also not a mandatory step but preferred.

In step 3, registration is performed after manual coarse segmentation of the prostate from the TRUS image is complete. The imported 3D prostate is aligned to match the 3D prostate created from manual coarse segmentation. This can be done manually and visually in the 3D visualization via a user interface for moving the imported 3D objects in 6-DOF, or automatically via a software routine that searches for the best fit of location and orientation of the imported 3D prostate to the 3D prostate created from coarse segmentation. The imported 3D objects including lesions or ROIs move with the imported 3D prostate. If the entire imported prostate was not segmented into a 3D object, at least three or more landmarks that are visible in the imported image and TRUS can be used for registration instead of the entire prostate. For example, the urethra ports at the base and apex of both the imported and coarse segmented prostate can be marked and used for registration, and a third readily identifiable landmark (possibly edges of seminal vesicles) can be used for registration. At the end of the registration step, the imported objects are added and imbedded into the prostate sensor space. The imported objects are tracked in prostate sensor space so that the imported objects move with the physical prostate as forces are applied to the tracked physical prostate from the TRUS probe.

Patient Care System in Simulation Mode. Training using new technology or equipment is often short-changed or an after-thought. To proactively plan for training in using our new technology, in one embodiment, the care system works with a PBx simulator 550, which can include an anatomical block made of plastic and ballistics gel in place of a patient for training purposes. The anatomical block simulates an anus, rectum, and/or prostate, as shown in FIG. 26 with a TRUS probe 120 inserted into it and oriented in left lateral decubitus position (photograph 460*a*) and in lithotomy position (photograph 460*b*). The simulator 550 contains reasonably realistic ultrasound-able ballistics gel that will create a usable TRUS image with a real TRUS probe 120 and a prostate made of ballistics gel that is tracked by the same or similar sensor (NDI Model 90 6-DOF electromagnetic sensor) as the prostate tracking sensor used in the care system. The system 100 can execute in simulation mode, such that the system 100 is not confused with a patient care mode by displaying a unique and highly visible label to clearly warn and indicate that the system 100 is in simulation mode, including a different border color and font so that the simulation mode is clearly recognizable from across the room while remaining functionally identical to the patent care mode.

Also, an inexpensive dummy TRUS probe 120 can be used (e.g., just the shell of an actual TRUS probe) and tracked with the TRUS probe clip. A TRUS image can then be generated by a software routine, as described above. An inexpensive dummy TRUS probe 120 in simulator mode reduces costs associated with using and cleaning a real TRUS machine and frees a real TRUS machine for clinical use.

Stand-Alone Simulator for Training. Another embodiment for training to use the care system is a stand-alone simulator that works independently of the patient care system and does not require an actual TRUS machine. All features described herein that are also applicable to a simulator 550 for training are also contemplated in the embodiments described herein, for instance, in the application domain of simulation technology, distinct from the patient care application. One difference is that the prostate tracking sensor is directly embedded into a physical 3D model (made, for example, of ballistic gel or silicone) of the prostate.

The tracking clips and cognitive aids (such as pitch, yaw, roll, insertion depth, template modification, maximum needle tip excursion, needle stop line, template location illumination, projected biopsy core, etc.) described above for patient care can also be used in simulation training. A synthetic TRUS image can be generated by computing in real time the intersection of a 2D insonation plane with virtual 3D objects. There is also a 6-DOF tracked tangible user interface to manually control the position of the virtual camera creating the perspective of the 3D visualization. The simulator includes a scoring algorithm that updates in real time and measures template deviation and allows placement of virtual cores, replay of previously placed cores or core sets with different sets of lesions of different shapes, sizes and positions and the calculation of prostate biopsy false negatives. The simulator can also import other 3D prostates from past patient scans.

For debriefing, after action review and performance analysis, the simulator can calculate the amount or percentage of lesion, prostatic tissue, and non-prostatic tissue (bladder, urethra, seminal vesicles, etc.) in each core. In one embodiment of the simulator, the tracking sensor is at the tip of the modified biopsy needle giving more reliable tracking of the needle tip given the long and flexible biopsy needle. The physical tracked prostate is located inside a cradle that allows the prostate to move within a circumscribed volume when pressure is applied to it via the TRUS probe 120 or via a digital rectal exam. The cradles are of standard size allowing cradles containing prostates of different sizes and shapes to be readily inserted into the corresponding standard receptacle in the prostate biopsy anatomical block. The simulator 550 can be used for transrectal (end-fire, side-fire) and transperineal needle biopsy, as shown in FIG. 26.

One or more sides of the anatomical block representing the rectum can be physically removed allowing direct visual observation of the TRUS probe 120 while it is in the rectal space and in contact with the prostate via the rectal wall. Users have found this feature useful. The simulator 550 can include a virtual coach for trainees that can also be used for the care system. The virtual coach can predict from the tracked TRUS probe 120, tracked biopsy needle and defined template or core positions the deviation that will occur. Using that prediction, the virtual coach can coach the trainee or practicing clinician to change for example the pitch or roll of the TRUS probe 120. The virtual coach can be rules-based (e.g., teach a pitch-neutral technique or be based on machine learning. In the latter case, the neural network is developed using Keras running under TensorFlow.

A deep learning neural networks (NNs) routine has been developed to predict core deviation from the template location and for coaching to reduce deviation. Neural networks other than deep learning NN can also be used. The two NNs (NNA1 and NNA2) use existing data from a PBx simulator 550, as shown in FIG. 26. Both NNA1 and NNA2 are feedforward multiple-layer perceptrons (MLPs) implemented in Keras running on TensorFlow.

NNA1 is a binary classification model that predicts if a simulated biopsy core that is about to be fired will be within or outside the acceptable template deviation of 5 mm. 3,216 simulated biopsy core records were used that contain biopsy deviation, intended template location, the tracked TRUS probe's pitch, yaw, roll, and insertion depth, and the tracked prostate position. A train/test split of 0.2 and a validation split of 0.2 can be used. In other words, the NNs can be trained with 80% of the data and the remaining 20% of the data was used to test the accuracy of the NN predictions. The records can be imported into pandas data frames and scaled using scikit-learn preprocessing libraries. Template deviation can be used as the target variable. Given only TRUS probe position, the tracked prostate position and the intended template location, NNA1 can predict in real time with no noticeable delay if the biopsy core will be good (template deviation <=5 mm) or bad (template deviation >5 mm) within 72% accuracy. A confusion matrix was generated along with a receiver operating characteristic (ROC) curve to illustrate the diagnostic ability of the binary classification system.

NNA2 is a regression model that uses the same inputs as NNA1 and predicts target deviation to within 3.46 mm. Both NNs using Keras running on Tensorflow were implemented using Python 3.7.4 (Python Software Foundation, Wilmington, DE) and pandas 1.0.1 (NumFOCUS, Austin TX) and scikit-learn 0.22.1 (Pedregosa et al). The accuracy of the NNs can be improved with more training data, additional inputs, and optimization. Such NNs can be used for coaching on the simulator 550 as well as during clinical use when biopsying actual patients. The neural network can be trained and repurposed to coach other guided interventions.

Marking Ends of Biopsy Cores. The ends of a real biopsy core may contain tissue that is sheared, distorted, mangled, or missing. In this case, the ends of the biopsy core may not be trusted to contain reliable or useful tissue for pathology exam. If the biopsy core has zones of low quality at one or both ends, user adjustable hash marks can be provided along the displayed length of the virtual biopsy core on the user interface. The hashmarks can also have default settings such as x mm from either end of the core, or x mm at leading (gets cut first) edge of the core and y mm at the trailing (gets cut last) edge of the core, instead of being user adjustable. The area between the two hashmarks indicates the area that can be more trusted to provide tissue that can be reliably used for pathology exam that represent the dimensions of the good or useable zone of the biopsy. There could also be only one hashmark on the core if only one end of the core is suspect, instead of both. The good region could also be denoted as a different color on the predicted virtual core. These hash marks can be visible in the 3D visualization, in the overlay on the output of an imaging device (such as a TRUS image), and in the biopsy template fitting, adjusting, and planning user interface. The center of the core can also be indicated as a different color hashmark on the line representing the core—the center of the core is generally in better condition than the ends and should therefore preferentially be placed at a lesion or suspected lesion site. For example, if 2 mm of the leading and trailing edges of an 18 mm long biopsy core are suspect to a pathologist, the user can consider a 14 mm long biopsy instead of the 18 mm long biopsy when planning core placement and during treatment.

Figure 27:
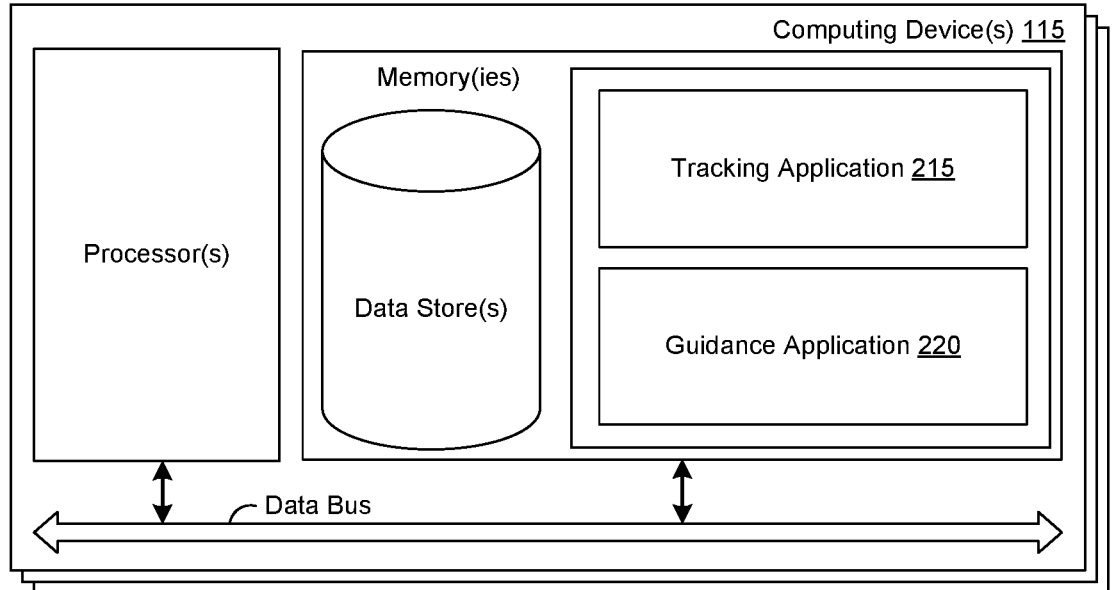
FIG. 27 is a schematic diagram of a computing device that may be employed for targeted biopsy and treatment in accordance with various embodiments of the present disclosure.

With reference to FIG. 27, shown is a schematic block diagram of the computing device 115 according to an embodiment of the present disclosure. The computing device 115 includes at least one processor circuit, for example, having a processor and a memory, both of which are coupled to a local interface. To this end, the computing device 115 may comprise, for example, at least one server computer, personal computing device, or like device. The local interface may comprise, for example, a data bus with an accompanying address/control bus or other bus structure as can be appreciated.

Stored in the memory are both data and several components that are executable by the processor. In addition, an operating system may be stored in the memory and executable by the processor. It is understood that there may be other applications that are stored in the memory and are executable by the processor as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, Unity 3D, or other programming languages.

A number of software components are stored in the memory and are executable by the processor. In this respect, the term "executable" means a program file that is in a form that can ultimately be run by the processor. Examples of executable programs may be, for example, a compiled program that can be translated into machine code in a format that can be loaded into a random access portion of the memory and run by the processor, source code that may be expressed in proper format such as object code that is capable of being loaded into a random access portion of the memory and executed by the processor, or source code that may be interpreted by another executable program to generate instructions in a random access portion of the memory to be executed by the processor, etc. An executable program may be stored in any portion or component of the memory including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory is defined herein as including both volatile and nonvolatile memory and data storage components. Volatile components are those that do not retain data values upon loss of power. Nonvolatile components are those that retain data upon a loss of power. Thus, the memory may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor may represent multiple processors and/or multiple processor cores and the memory may represent multiple memories that operate in parallel processing circuits, respectively. In such a case, the local interface may be an appropriate network that facilitates communication between any two of the multiple processors, between any processor and any of the memories, or between any two of the memories, etc. The local interface may comprise additional systems designed to coordinate this communication, including, for example, performing load balancing. The processor may be of electrical or of some other available construction.

Although the various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc.

The flowcharts of FIGS. 4, 16, and 20 show the functionality and operation of an implementation of portions of the computing device 115. If embodied in software, each block may represent a segment or portion of code that comprises program instructions to implement the specified logical function(s). The program instructions may be embodied in the form of source code that comprises human-readable statements written in a programming language or machine code that comprises numerical instructions recognizable by a suitable execution system such as a processor in a computer system or other system. The machine code may be converted from the source code, etc. If embodied in hardware, each block may represent a circuit or a number of interconnected circuits to implement the specified logical function(s).

Although the flowcharts of FIGS. 4, 16, and 20 show a specific order of execution, it is understood that the order of execution may differ from that which is depicted. For example, the order of execution of two or more blocks may be scrambled relative to the order shown. Also, two or more blocks shown in succession in FIGS. 4, 16, and 20 may be executed concurrently or with partial concurrence. Further, in some embodiments, one or more of the blocks shown in FIGS. 4, 16, and 20 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that comprises software or code can be embodied in any non-transitory computer-readable medium for use by or in connection with an instruction execution system such as, for example, a processor in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device 115, or in multiple computing devices in the same computing environment. Additionally, it is understood that terms such as "application," "service," "system," "engine," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A tracking and guidance system, comprising:
a body organ electromagnetic tracking sensor;
a tracked medical imaging device; an electromagnetically tracked biopsy or treatment device;
at least one computing device comprising program instructions stored in memory thereon that, when executed, direct the at least one computing device to:
obtain positions and orientations of a body organ with the body organ electromagnetic tracking sensor, the tracked medical imaging device, and the electromagnetically tracked biopsy or treatment device;
generate a plurality of images of an organ tracked by the body organ electromagnetic tracking sensor, based at least on a position and an orientation of the tracked medical imaging device relative to the body organ electromagnetic tracking sensor;
generate a three-dimensional reconstruction of at least one of the body organ or a feature associated therewith using the plurality of images and respective positions and orientations of the tracked medical imaging device;
provide a three-dimensional perspective visualization, the three-dimensional perspective visualization contemporaneously comprising: (a) the three-dimensional reconstruction of at least one body organ or a feature associated therewith, (b) the tracked medical imaging device, (c) the electromagnetically tracked biopsy or treatment device, and (d) a visual indication of one or more imaging planes;
provide, contemporaneously with the three-dimensional perspective visualization comprising the three-dimensional reconstruction, the tracked medical imaging device, the electromagnetically tracked biopsy or treatment device, and the visual indication of one or more imaging planes, one or more two-dimensional images generated based on one or more images acquired along the one or more imaging planes; and
provide guidance via the three-dimensional perspective visualization and the one or more two-dimensional images for at least one of a biopsy or a treatment.

2. The tracking and guidance system of claim 1, wherein the plurality of images comprises a plurality of two-dimensional ultrasound images.

3. The tracking and guidance system of claim 1, wherein:
the tracked medical imaging device is a transrectal ultrasound probe; and
the body organ comprises a prostate and the guidance is performed during a prostate biopsy procedure.

4. The tracking and guidance system of claim 1, wherein the three-dimensional reconstruction is generated using the body organ electromagnetic tracking sensor, positioned outside of a body of a patient having the organ.

5. The tracking and guidance system of claim 1, wherein the body organ electromagnetic tracking sensor is a tracking sensor having six degrees-of-freedom (6-DOF).

6. The tracking and guidance system of claim 1, wherein the body organ electromagnetic tracking sensor is positioned in a patient having the body organ.

7. The tracking and guidance system of claim 1, wherein the three-dimensional reconstruction comprises a three-dimensional reconstruction of a lesion, cavity, abscess, or region of interest detected on the organ or imported into the organ.

8. The tracking and guidance system of claim 1, wherein the at least one computing device is further directed to perform:
fit the three-dimensional reconstruction of the organ or the feature associated therewith to a virtual template comprising at least one three-dimensional core;
perform at least one of adjusting core and template locations and orientations, adjusting a number of cores, and changing a sequence of cores in a custom template.

9. The tracking and guidance system of claim 1, wherein the guidance is provided at least one sampling region associated with at least one three-dimensional core and is provided without an imaging modality, wherein the imaging modality is not needed with respect to the three-dimensional reconstruction.

10. A method, comprising:
providing a body organ electromagnetic tracking sensor, a tracked medical imaging device, an electromagnetically tracked biopsy or treatment device, and at least one computing device;
obtain positions and orientations of a body organ with the body organ electromagnetic tracking sensor, the tracked medical imaging device, and the electromagnetically tracked biopsy or treatment device;
generate a plurality of images of an organ tracked by the body organ electromagnetic tracking sensor, based at least on positions and orientations of the tracked medical imaging device relative to the body organ electromagnetic tracking sensor;

generating a three-dimensional reconstruction of the organ or an associated feature using the plurality of images and respective positions and orientations of the tracked medical imaging device when the plurality of images were captured:

providing a three-dimensional perspective visualization, the three-dimensional perspective visualization contemporaneously comprising: (a) the three-dimensional reconstruction of at least one of the body organ or a feature associated therewith, (b) the tracked medical imaging device, (c) the electromagnetically tracked biopsy or treatment device, and (d) a visual indication of one or more imaging planes;

providing, contemporaneously with the three-dimensional perspective visualization comprising the three-dimensional reconstruction, the tracked medical imaging device, the electromagnetically tracked biopsy or treatment device, and the visual indication of one or more imaging planes, one or more two-dimensional images generated based on one or more images acquired along the one or more imaging planes; and providing guidance via the three-dimensional perspective visualization and the one or more two-dimensional images for at least one of a biopsy or a treatment.

11. The method of claim 10, wherein the plurality of images are a plurality of two-dimensional ultrasound images.

12. The method of claim 11, further comprising: displaying at least one of the plurality of two-dimensional ultrasound images contemporaneously with the three-dimensional reconstruction of the organ in a three-dimensional visualization of the electromagnetically tracked biopsy or treatment device.

13. The method of claim 12, wherein:

the tracked medical imaging device is a transrectal ultrasound probe; and the organ comprises a prostate and the guidance is performed during a prostate biopsy procedure.

14. The method of claim 10, wherein:

the three-dimensional reconstruction of at least one of the body organ or the feature associated therewith is generated using the body organ electromagnetic tracking sensor positioned inside of a body of a patient having the organ, and the body organ electromagnetic tracking sensor has six degrees-of-freedom (6-DOF).

15. The method of claim 10, wherein the body organ electromagnetic tracking sensor is a tracking sensor having six degrees-of-freedom (6-DOF).

16. The method of claim 10, wherein the body organ electromagnetic tracking sensor is positioned in a patient having the organ.

17. The method of claim 10, wherein the three-dimensional reconstruction comprises a three-dimensional reconstruction of a lesion, cavity, or region of interest detected on the organ or imported into the organ.

18. The method of claim 10, wherein the at least one computing device is further directed to perform:

fit the three-dimensional reconstruction of the organ or the feature associated therewith to a virtual template comprising at least one three-dimensional core; and perform at least one of adjusting core and template locations and orientations, adjusting a number of cores, and changing a sequence of cores in a custom template.

19. The method of claim 18, wherein the guidance for treatment or collection of tissue or fluid is provided at least one sampling region associated with the at least one three-dimensional core and without an imaging modality, wherein the imaging modality is not needed during a biopsy or a treatment applied using the three-dimensional reconstruction.

20. The method of claim 10, wherein an edge of one or more of the one or more imaging planes in the three-dimensional perspective visualization is visually consistent with respective edges of the one or more imaging planes in the one or more two-dimensional images.

\* \* \* \* \*